(12) United States Patent
Crapo et al.

(10) Patent No.: US 6,479,477 B1
(45) Date of Patent: *Nov. 12, 2002

(54) SUBSTITUTED PORPHYRINS

(75) Inventors: James D. Crapo, Englewood, CO (US); Brian J. Day, Englewood, CO (US); Polivina Jolicia F. Gauuan, Albany, NY (US); Anthony D. Pechulis, Jr., Guilderland, NY (US); Michael P. Trova, Schenectady, NY (US)

(73) Assignees: Duke University, Durham, NC (US); Aeolus Pharmaceuticals, Inc., Research Triangle Park, NC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/296,615

(22) Filed: Apr. 23, 1999

Related U.S. Application Data

(60) Provisional application No. 60/082,881, filed on Apr. 24, 1998.

(51) Int. Cl.[7] .......................... A61K 51/04; C07D 487/22
(52) U.S. Cl. .......................... 514/183; 514/410; 540/145
(58) Field of Search .................... 540/145; 514/183, 514/410

(56) References Cited

U.S. PATENT DOCUMENTS

| | | | |
|---|---|---|---|
| 2,951,799 A | 9/1960 | Sharp | 204/162 |
| 4,614,723 A | 9/1986 | Schmidt | 436/436 |
| 4,746,735 A | 5/1988 | Kruper, Jr. et al. | 540/145 |
| 4,758,422 A | 7/1988 | Quay | 424/9 |
| 4,837,221 A | 6/1989 | Bonnett | 514/410 |
| 4,851,403 A | 7/1989 | Picker et al. | 514/185 |
| 4,885,114 A | 12/1989 | Gordon et al. | 252/589 |
| 4,892,941 A | 1/1990 | Dolphin et al. | 540/145 |
| 4,895,719 A | 1/1990 | Radhakrishnam | 424/45 |
| 5,171,680 A | 8/1990 | Mullenbach et al. | 435/189 |
| 4,963,367 A | 10/1990 | Ecanow | 424/485 |
| 5,051,337 A | 9/1991 | Sakoda et al. | 430/270 |
| 5,130,245 A | 7/1992 | Marklund et al. | 435/189 |
| 5,162,519 A | 11/1992 | Bonnett | 514/185 |
| 5,169,630 A | 12/1992 | Okaya et al. | 424/401 |

(List continued on next page.)

FOREIGN PATENT DOCUMENTS

| | | |
|---|---|---|
| EP | 0 127 797 | 12/1984 |
| EP | 0 186 962 | 7/1986 |
| EP | 0 282 899 | 9/1988 |
| EP | 0 336 879 | 10/1989 |
| EP | 0 337 601 | 10/1989 |
| EP | 0 345 171 | 12/1989 |
| EP | 0 414 915 A1 | 3/1991 |
| EP | 0 462 836 | 12/1991 |
| EP | 0 524 161 A1 | 1/1993 |
| EP | 0 532 327 | 3/1993 |
| FR | 2 676 738 | 11/1992 |
| WO | WO 91/04315 | 4/1991 |
| WO | WO 92/07935 | 5/1992 |
| WO | WO 92/15099 | 9/1992 |
| WO | WO 93/02090 | 2/1993 |
| WO | WO 94/04614 | 3/1994 |
| WO | WO 95/10185 | 4/1995 |
| WO | WO 95/31197 | 11/1995 |
| WO | WO 9609038 | 3/1996 |
| WO | WO 96/09053 | 3/1996 |
| WO | WO 96/40223 | 12/1996 |
| WO | WO 98/33503 | 6/1998 |
| WO | WO 99/23097 | 5/1999 |
| WO | WO 99/55388 | 11/1999 |
| WO | WO 00/43395 | 7/2000 |
| WO | WO 01/26655 | 4/2001 |
| WO | WO 01/96345 | 12/2001 |

OTHER PUBLICATIONS

Collman et al. J. Am. Chem. Soc. 103(3) (1981) 516–533.*
Batinić –Haberle Arch. Biochem. Biophys. 343(2) (1997) 225–233.*
Comhair et al. Lancet 355(9204) (2000) 624 (Medline abstract).*
Rosenfeld et al. Pediatrics 6 (1996) 811–817 (Medline abstract).*
Lee et al. J. Chem. Soc., Perkin Trans. 1 (1997) 1215.*
Freeman and Crapo, "Biology of disease: free radicals and tissue injury", Lab. Invest. 47(5):412–426 (1982)—Abstract.

(List continued on next page.)

*Primary Examiner*—Richard L. Raymond
(74) *Attorney, Agent, or Firm*—Nixon & Vanderhye P.C.

(57) ABSTRACT

The present invention relates, in general, to a method of modulating physiological and pathological processes and, in particular, to a method of modulating cellular levels of oxidants and thereby processes in which such oxidants are a participant. The invention also relates to compounds and compositions suitable for use in such methods. Compounds of the invention include those of Formula I.

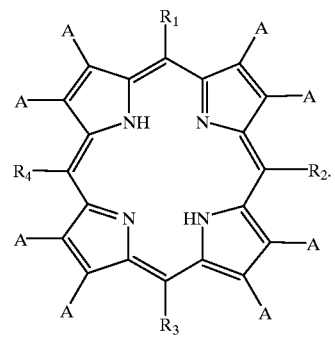

23 Claims, 3 Drawing Sheets

U.S. PATENT DOCUMENTS

| | | | |
|---|---|---|---|
| 5,202,317 A | 4/1993 | Bruice | 514/189 |
| 5,217,966 A | 6/1993 | Bruice | 514/189 |
| 5,223,538 A | 6/1993 | Fridovich | 514/616 |
| 5,227,405 A | 7/1993 | Fridovich | 514/612 |
| 5,236,914 A | 8/1993 | Meunier | 514/185 |
| 5,236,915 A | 8/1993 | Fiel | 514/185 |
| 5,248,603 A | 9/1993 | Marklund et al. | 435/189 |
| 5,262,532 A | 11/1993 | Tweedle et al. | 540/145 |
| 5,281,616 A | 1/1994 | Dixon et al. | 514/410 |
| 5,284,647 A | 2/1994 | Niedballa | 424/81 |
| 5,366,729 A | 11/1994 | Marklund et al. | 424/94.4 |
| 5,472,691 A | 12/1995 | Marklund et al. | 424/94.4 |
| 5,493,017 A | 2/1996 | Therien et al. | 540/142 |
| 5,599,924 A | 2/1997 | Therien et al. | 540/145 |
| 5,674,467 A | 10/1997 | Maier et al. | 424/1.65 |
| 5,747,026 A | 5/1998 | Crapo | 424/94.3 |
| 5,994,339 A | 11/1999 | Crapo et al. | 514/185 |
| 6,046,188 A | 4/2000 | Malfroy-Camine et al. | 514/185 |
| 6,084,093 A | 7/2000 | Riley et al. | 540/645 |
| 6,103,714 A | 8/2000 | Fridovich et al. | 514/185 |
| 6,127,356 A | 10/2000 | Crapo et al. | 514/185 |

OTHER PUBLICATIONS

Pietarinen et al, "Catalase and glutathione reductase protection of human alveolar macrophages during oxidant exposure in vitro", Am. J. Respir. Cell Mol. Biol. 13(4):434–441 (1995)—Abstract.

Poli, G., "Pathogenesis of liver fibrosis" role of oxidative stress", Mol. Aspects Med. 21(3):49–98 (2000)—Abstract.

Delanty and Dichter, "Antioxidant therapy in neurologic disease", Arch. Neurol. 57(9):1265–1270 (2000)—Abstract.

Smith et al, "Oxidative stress in Alzheimer's disease", Biochim. Biophy. Acta 1502(1):139–144 (2000)—Abstract.

Zalba et al, "Vascular oxidant stress: molecular mechanisms and pathophysiological implications", J. Physiol. Biochem. 56(1):57–64 (2000)—Abstract.

Babior, B.M., "Phagocytes and oxidative stress", Am. J. Med. 109(10:33–44 (2000)—Abstract.

Dhalla et al, "Status of myocardial antioxidants in ischemia–reperfusion injury", Cardiovasc. Res. 47(3):446–456 (2000)—Abstract.

Dhalla et al, "Role of oxidative stress in cardiovascular diseases", J. Hypertens. 18(6):655–673—Abstract (2000).

Sohal et al, "Current issues concerning the role of oxidative stress in aging: a perspective", Results Probl. Cell Differ. 29:45–66 (2000)—Abstract.

Melov, S., "Mitochondrial oxidative stress. Physiologic consequences and potential for a role in aging", Ann. N.Y. Acad. Sci. 908:219–225 (2000)—Abstract.

Laight et al, "Antioxidants, diabetes and endothelial dysfunction", Cardiovasc. Res. 47(3):457–464 (2000)—Abstract.

Grune et al, "Oxidative stress in anemia", Clin. Nephrol. 53(1 Suppl):S18–22 (2000)—Abstract.

Mates and Sanchez–Jimenez, "Role of reactive oxygen species in apoptosis: implications for cancer therapy", Int. J. Biochem. Cell Biol. 32(2):157–170 (2000)—Abstract.

Mates et al, "Antioxidant enzymes and human diseases", Clin. Biochem. 32(8):595–603 (1999)—Abstract.

Battino et al, "Oxidative injury and inflammatory periodontal diseases: the challenge of anti–oxidants to free radicals and reactive oxygen species", Crit. Rev. Oral Biol. Med. 10(4):458–476 (1999)—Abstract.

Simonson et al, "Aerosolized manganese SOD decreases hyperoxic pulmonary injury in primates. I. Physiology and biochemistry", J. Appl. Physiol. 83(2):550–558 (1997)—Abstract.

Welty–Wolf et al, "Aerosolized manganese SOD decreases hyperoxic pulmonary injury in primates, II. Morphometric analysis", J. Appl. Physiol 83(2):559–568 (1997)—Abstract.

Hertz and Cloarec, "Pharmacology of free radicals; recent views on their relation to inflammatory mechanisms", Life Sci. 34(8):713–720 (1984)—Abstract.

Esterbauer et al, "The role of lipid peroxidation and antioxidants in oxidative modification of LDL", Free Radic. Biol. Med. 134(4):341–390 (1992)—Abstract.

Hall and Braughler, "Central nervous system trauma and stroke. II. Physiological and pharmacological evidence for involvement of oxygen radicals and lipid peroxidation", Free Radic. Biol. Med.6(3):303–313 (1989)—Abstract.

Loeper et al, "Lipid peroxidation and protective enzymes during myocardial infarction", Clin. Chim. Acta 196(2–3):119–125 (1991)—Abstract.

Galley et al, "Total antioxidant capacity and lipid peroxidation during liver transplantation", Clin. Sci. (Lond) 89(3):329–332 (1995)—Abstract/

Day et al, "Metalloporphyrins are potent inhibitors of lipid peroxidation", Free Radic. Biol. Med. 26(5–6):730–736 (1999)—Abstract.

Sheldon, Chapter 1 in Metalloporphyrins in Catalytic Oxidations, Marcel Dekker, Inc. (1994).

Bors et al, "An expanded function for superoxide dismutase", Free Radic. Res. Commun. 12–13 Pt. 1:411–417 (1991)—Medline Abstract.

Crapo and Tierney, "Superoxide dismutase and pulmonary oxygen toxicity", American Journal of Physiology 226(6):1401–1407 (1974).

O'hara et al, "Potentiation of radiation–induced cell kill by synthetic metalloporphyrins", Int. J. Radiat. Oncol. Biol. Phys. 16(4):1049–1052 (1989).

Lee et al, "Rapid decomposition of peroxynitrite by manganese porphyrin–antioxidant redox couples", Bioorganic & Medical Chemistry Letters 7(22):2913–2918 (1997).

Madakyan et al, "New watersoluble metal complexes of meso–tetrakis[3–N–(2'–hydroxy ethyl)pyridyl]porphyrins and their pharmacological activity", Arm Khim. Zh. 42(11):724–728—Chemical Abstracts 113:653—Abstract No. 114907h (1990).

Wheelhouse et al, "Cationic Porphyrins as Telomerase Inhibitors; the Interaction of Tetra–(N–methyl–4–pyridyl)-porphine with Quadruplex DNA", J. Am. Chem. Soc. 120(13):3261–3262 (1998).

Zahedi, "Semiempirical molecular orbital calculations of biliverdin: study of dynamics and energetics of the self–association of a two–electron oxidation product", Theochem. 531:79–88 (2000).

Lord, "Redox characteristics of nickel and palladium complexes of the open–chain tetrapyrrole octaethylbilindione: a biliverdin model", Inorg. Chem. 39(6):1128–1134 (2000).

Balch, "Isolation and characterization of an iron biliverdin–type complex that is formed along with verdohemochrome during the coupled oxidation of iron (II) octaethylporphyrin", Am. Chem. Soc. 115(20):9056–9061 (1993).

Koerner, "Carbon monoxide production during the oxygenation of cobalt complexes of linear etrapyrroles", Inorg. Chem. 37(5):982–988 (1998).

Balch, "Solid–state self–association of the two–electron oxidation product of a biliverdin analogue", J. Chem. Soc. Chem. Commun. 6:643–644 (1995).

Balch, "Geometric and electronic structure and dioxygen sensitivity of the copper complex of octaethylbilindione, a biliverdin analog", J. Am. Chem. Soc. 115(25):12206–12207 (1993).

Falk, "Constributions to the chemistry of pyrrolic pigments", Tetrahedron 37(4):761–767 (1981).

Burke, "Photochemical and thermal transformations of phytochrome", Chem. Physiol. Bile Pigm., Int. Symp., pp. 509–517 (1975).

Crapo et al, 721195, Document No. 123 :218443 (1995).

Butje et al, "Electronic Spectra, Resonance Raman Spectra and Solution Properties of Water–soluble (Cu(II), Ni(II) and Co(III) Porphyrins", Inorg. Chim. Acta 167:97–108 (1990).

Davila et al, "Sterically–Hindered Zinc Porphyrins for Solar–Energy Conversion", J. Chem. Soc., Chem. Commun., pp. 525–527 (1987).

Kaufmann et al, "Separation of the Rotational Isomers of Tetrakis(N–methyl–2–pyridiniumyl)porphyrin and Crystal Sturcture of α, α, α, β–(Tetrakis(N–methyl–2–pyridiniumyl)porphyrin)copper Hexacyanoferrate", Inorg. Chem. 34:5073–5079 (1995).

Sari et al, "Interaction of Cationic Porphyrins with DNA: Importance of the Number and Position of the Charges and Minimum Structural Requirements for Intercalation", Biochemistry 29:4205–4215 (1990).

Vodzinskii et al, "Porphyrines and Their Derivatives. XX. Synthesis and Properties of 2–Nitro–5,10,15,20–tetraheterylporphyrins", Russian Journal of Organic Chemistry 34(6):882–885 (1998).

Hambright et al, "Manganese(III) porphyrin isomers: polarography and stannous ion reduction kinetics", Porphyrin Chem. Adv., editor: Longo, [Pap. Porphyrin Symp.], pp. 284–292, Meeting Date 1977.

Tjahjono et al, "Cationic porphyrins bearing diazolium rings: synthesis and their interaction with calf thymus DNA", Biochemica et Biophisica Acta 1472:333–343 (1999).

Callot and Schaeffer, "Ring contraction of homoporphyrins to porphyrins, meso–Reactivity of 5,10,15–Triphenylporphin and Porphin", J. Chem. Research (S):51 (1978).

Inoue et al, "Expression of a Hybrid Cu/Zn–type Superoxide . . . ," J. Bio. Chem., vol. 266, No. 25, pp. 16409–16414 (1991).

Day et al, "Manganic Porphyrins Possess Catalase Activity . . . ," Arch. Biochem. Biophys., vol. 347, No. 2, pp. 256–262 (1997).

Tsan, M–F., "Superoxide Dismutase and Pulmonary Oxygen Toxicity," XP–002074505, pp. 286–290 (1993).

Foran et al, "Effect of Electrolyte Concentration on Axial Anion Ligation in Manganese(III) Meso–Tetraphenylporphyrin Chlorides", Inorg. Chem. 31:1463–1470 (1992).

Milgrom, Facile Aerial Oxidation of a Porphyrin. Part 3. Some Metal Complexes of meso–Tetrakis–(3, 5–di–t–butyl–4–hydroxyphenyl)porphyrin, J. Chem. Soc. Perkin Trans. 11:71–79 (1988).

Bockhorst and Hoehn–Berlage, "An Optimized Synthesis of Manganese meso–Tetra(4–sulfonato–phenyl)porphine: A Tumor–Selective MRI Contrast Agent", Tetrahedron 50(29):8657–8660 (1994).

Keinan et al, "Catalytic Antibodies. Circular Dichroism and UV–Vis Studies of Antibody–Metalloporphyrin Interactions", Inorg. Chem. 31:5433–5438 (1992).

Marx, "Role of Gene Defect in Heredity ALS Clarified", Science 261:986 (1993).

Epp et al, "Superoxide Dismutase Activity of Manganese Chelates", 76–78 (1986).

Milgrom et al, "Redox Behaviour of Phenolic Porphyrins in Basic Solutions: A Reappraisal", Free Rad. Res. 24(1):19–29 (1996).

Szabo et al, "Evaluation of the relative contribution of nitric oxide and peroxynitrite to the suppression of mitochondrial respiration in immunostimulated macrophages using a manganese mesoporphyrin superoxide dismutase mimetic and peroxynitrite scavenger", FEBS Letters 381:82–86 (1996).

Patel et al, "Requirement for Superoxide in Excitotoxic Cell Death", Neuron 16:345–355 (1996).

Bamford et al, "The Squalestatins: Synthesis and Biological Activity of Some C3–Modified Analogues; Replacement of a Carboxylic Acid or Methyl Ester with an Isoelectric Heterocyclic Functionality", J. Med. Chem. 38:3502–3513 (1995).

Szabo et al, "Peroxynitrite Is Involved in the Pathogenesis of the Vascular Contractile and Energetic Failure in Endotoxic Shock", Shock Society Meeting (1996).

Stralin et al, "Effects of Oxidative Stress on Expression of Extracellular Superoxide Dismutase, CuZn–Superoxide Fibroblast", Biochem. J. 298:347–352 (1994).

Folz et al, "Extracellular Superoxide Dismutase (SOD3):Tissue–Specific Expression, Genomic Characterization, and Computer–Assisted Sequence Analysis of the Human EC SOD Gene", Genomics 22:162–171 (1994).

Clyde et al, "Distribution of Manganese Superoxide Dismutase mRNA in Normal and Hyperoxic Rat Lung", American Journal of Respiratory Cell and Molecular Biology 8:530–537 (1993).

Wolberg et al, Electrocical and Electron Paramagnetic Resonance Studies of Metalloporphyrins and Their Electrochemical Oxidation Products:, Journal of the American Chemical Society 92(10):2982–2990 (1970).

Pasternack et al, "Superoxide Dismutase Activities of an Iron Porphyrin and Other Iron Complexes", Journal of the American Chemical Society 101(4):1026–1031 (1979).

Winkelman, James, "The Distribution of Tetraphenylporphinesulfonate in the Tumor–bearing Rat", Cancer Research 22:589–596 (1962).

Moisy et al, "Catalytic Oxidation of 2,6–Di–Terbutylphenol by Molecular Oxygen Electroassisted by Poly(Pyrrole–Manganese–Porphyrin)", New J. Chem. 13:511–514 (1989).

Malinski et al, "Characterization of Conductive Polymeric Nickel(II) Tetrakis(3–methoxy–4–hydroxy–phenyl)Porphyrin as an Anodic Material for Electrocatalysis", J. Electrochem. Soc. 138(7):2008–2015 (1991).

Weinraub et al, "Chemical properties of water–soluble porphyrins. 5. Reactions of some manganese (III) porphyrins with the superoxide and other reducing radicals", Int. J. Radiat. Biol. 50(4):649–658 (1986) (Abs).

Fajer et al, "π–Cation Radicals and Dications of Metalloporphyrins", Journal of the American Chemical Society 92(11):3451–3459 (1970).

Pasternack et al, "Aggregation of Nickel(II), Coppwer (II), and Zinc(II) Derivatives of Water–Soluble Porphyrins", Inorganic Chemistry 12(11):2606–2610 (1973).

Datta–Gupta et al, "Synthetic Porphyrins. I. Synthesis and Spectra of Some *para*–Substituted *meso*–Tetraphenylporphines (1)", J. Heterocycl. Chem. 3:495–502 (1966).

Harriman et al, "Photochemistry of Manganese Porphyrins Part 2.–Photoreduction", pp. 1543–1552 (1979).

Longo et al, "The Synthesis and Som e Physical Properties of *ms*–Tetra(pentafluorophenyl)–porphin and *ms*–Tetraphenylporphines (1)", Notes 6:927–931 (1969).

Barnitz–McLaughlin et al, "Reactions of Fe$^{III}$(*meso*–α,α, α, α–tetrakis[O–[N–methylisonicotinamido)phenyl]porphyrin)$^{5+}$ and Fe$^{III}$(*meso*–tetrakis[N–methylpyridinium–4–yl] porphyrin)$^{5+}$ with NC$^-$, CO$_2^{-}$", Inorg. Chem. 32:941–947 (1993).

Pasternack et al, "On the Aggregation of Meso–Substituted Water–Soluble Porphyrins", Journal of American Chemical Society 94(13):4511–4517 (1972).

Datta–Gupta et al, "Synthetic Porphyrins II Preparation and Spectra of Some Metal Chelates of *para*", Journal of Substituted–*mesa*–Tetraphenylporphines, J. of Pharmaceutical Science 57(2):300–304 (1968).

Boissinot et al, "Rational Design and Expression of a Heparin–Targeted Human Superoxide Dismutase", Biochemical and Biophysical Research Communication 190(1):250–256 (1993).

Oury et al, "Cold–induced Brain Edema in Mice", The Journal of Biological Chemistry 268(21):15394–15398 (1993).

Oury et al, "Extracellular superoxide dismutase, nitric oxide, and central nervous system O$_2$ toxicity", Proc. Natl. Acad. Sci. USA 89:9715–9719 (1992).

Pasternack et al, "Catalyst of the Disproportionation of Superoxide by Metalloporphyrins III", Journal of Inorganic Biochemistry 15:261–267 (1981).

Oury et al, "Establishment of Transgenic Mice Expressing Human Extracellular Superoxide Dismutase", American Review of Respiratory Disease 143(4):A515 (1991), International Conference Supplement Abstracts—No. 236.

Oury et al, "Transgenic Mice Superexpressing Human Extracellular Superoxide Dismutase Show Increased Resistance to Cold–induced Brain Edema, But are More Susceptible to Hyperbaric Oxygen", American Review of Respiratory Disease 145(4):A713 (1992), International Conference Supplement Abstracts—No. 211.

Oury et al, "Immunocytochemical Localization of Extracellular Superoxide Dismutase in Human Lung", American Review of Respiratory Disease 147(4):A713 (1993), International Conference Supplement Abstracts—No. 246.

Oury, Tim D., "Extracellular Superoxide Dismutase and Nitric Oxide: Transgenic and Immunocytochemical Studies", Dissertation submitted in partial fulfillment of the requirements for the degree of Doctor of Philosophy in the Department of Pathology in the Graduate School of Duke University (Jun. 17, 1993).

Gosh, "Substituent Effects on Valence Ionization Potentials of Free Base Porphyrins: Local Density Functional Calculations and Their Relevance of Electrochemical and Photelectron Spectroscopic Studies", J. Am. Chem. Soc. 117:4691–4699 (1995).

De Peretti et al, "Imidazol[2,1–b]benzoxazole–3–acetamide derivatives, their preparation, and their therapeutic use", Chemical Abstracts 121:1016, Abstract No. 121:200896u (1994).

Oberley et al, "Anticancer activity of metal compounds with superoxide dismutase activity", Agents and Actions 15(5/6):535–538 (1984).

Collman et al, "Synthesis of "Face to Face" Porphyrin Dimers Linked by 5,15–Substituents: Potential Binuclear Multielectron Redox Catalysts", J. Am. Chem. Soc. 103:516–533 (1981).

Gassman et al, "Electronic Effects of Peripheral Substituents in Porphyrins: X–ray Photoelectron Spectroscopy and ab Initio Self–Consistent Field Calculations", J. Am. Chem. Soc. 114:9990–10000 (1992).

Bishop et al, "The Reaction of Thiomides with Phosphorus Ylides", J. Org. Chem. 56:5079–5091 (1991).

Picker et al, "Cobalt(III) complexes of water soluble synthetic meso–substituted porphyrins as radiation sensitizers for oxic and hypoxic tumor cells", 8–Radiation 112:405 (1990) Abstract No. 112:73026d.

McCord et al, "Superoxide Dismutase–An Enzymic Function for Erythrocuprein", Biochemisty 492, p. 346 (1968).

McCord et al, Superoxide Dismutase An Enzymic Function for Erythrocuprein (Hemocuprein), The Journal of Biological Chemistry 244(22):6049–6055 (1969).

Crapo et al, "Superoxide Dismutase and Oxygen Toxicity", Clinical Research, p. 222 (1977).

Crapo et al, "The Failure of Aerosolized Superoxide Dismutase to Modify Pulmonary Oxygen Toxicity", American Review of Respiratory Disease 115:1027–1033 (1977).

Joester et al, "Superoxide Dismutase Activity of Cu$^{2+}$–Amino Acid Chelates", FEBS Letters 25(1):25–28 (1972).

Brigelius et al, "Superoxide Dismutase Activity of Low Molecular Weight Cu2+–Chelates Studied by Pulse Radiolysis", FEBS Letters 47(1):72–75 (1974).

Sorenson, John R.J., "Copper Chelates as Possible Active Forms of the Antiarthritic Agents", Journal of Medicinal Chemistry 19(1):135–148 (1976).

deAlvare et al, "Mechanism of Superoxide Anion Scavenging Reaction by Bis–(Salicylato)–Copper(II) Complex", Biochemical and Biophysical Research Communications 69(3):687–694 (1976).

Halliwell, Barry, "The Superoxide Dismutase Activity of Iron Complexes", FEBS Letters 56(1):34–38 (1975).

McClune et al, "Catalysis of Superoxide Dismutation by Iron–Ethylenediaminetetraacetic Acid Complexes. Mechanism of the Reaction and Evidence for the Direct Formation of an Iron(III)–Ethylenediaminetetraacetic Acid Peroxo Complex from the Reaction of Superoxide with Iron(II)–Ethylenediaminetetraacetic Acid", Communications to the Editor, pp. 5220–5222 (1977).

Diguiseppi et al, "Putative Superoxide Dismutase Activity of Iron–EDTA: A Reexamination", Archives of Biochemistry and Biophysics 203(1):145–150 (1980).

Robertson, Jr. Et al, "Does Copper–D–Penicillamine Catalyze the Dismutation of O$_2^{-}$?", Archives of Biochemistry and Biophysics 203(2):830–831 (1980).

Werringloer et al, "The Integration of Divalent Copper and the Microsomal Electron Transport System", The Journal of Biological Chemistry, 254(23):11839–11846 (1979).

Pasternack et al, "Catalyst of the Disproportionation of Superoxide by Metalloporphyrins", Journal of Inorganic Biochemistry 11:261–267 (1979).

Archibald et al, Manganese and Defenses against Oxygen Toxicity in *Lactobacillus plantarum*, Journal of Bacteriology 145(1):442–451 (1981).

Archibald et al, Manganese, Superoxide Dismutase, Oxygen Tolerance in Some Lactic Acid Bacteria, Journal of Bacteriology 146(3):928–936 (1981).

Archibald et al, The Scavenging of Superoxide Radical by Manganous Complex: In Vitro, Archives of Biochemistry and Biophysics 214(2):452–463 (1982).

Archibald et al, Investigations of the State of the Manganese in *Lactobacillus plantarum*, Archives of Biochemistry and Biophysics 215(2):589–596 (1982).

Darr et al, "A Mimic of Superoxide Dismutase Activity Based Upon Desferrioxamine B and Manganese(IV)", Archives of Biochemistry and Biophysics 258(2):351–355 (1987).

Beyer, Jr., Characterization of a Superoxide Dismutase Mimic Prepared from Desferrioxamine and $MnO_2$, Archives of Biochemistry and Biophysics 271(1):149–156 (1989).

Faulkner et al, "Characterization of Mn(III) Complexes of Linear and Cyclic Desferrioxamines as Mimics of Superoxide Dismutase Activity", Archives of Biochemistry and Biophysics 310(2):341–346 (1994).

Faulkner et al, Stable Mn(III) Porphyrins Mimic Superoxide Dismutase in Vitro and Substitute for It in Vivo, The Journal of Biological Chemistry 269(38):23471–23476 (1994).

Liochev et al, "A Cationic Manganic Porphyrin Inhibits Uptake of Paraquat by *Escherichia coli*", Archives of Biochemistry and Biophysics 321(1):271–275 (1995).

Peretz et al, "Chemical properties of water–soluble porphyrins 3. The reaction of superoxide radicals with some metalloporphyrins", Int. J. Radiat. Biol. 42(4):449–456 (1982).

Baudry et al, "Salen–Manganese Complexes are Superoxide Dismutase–Mimics", Biochemical and Biophysical Research Communication 192(2):964–968 (1993).

Gonzalez et al, "EUK–8, a Synthetic Superoxide Dismutase and Catalase Mimetic, Ameliorates Acute Lung Injury in Endotexemic Swine", The Journal of Pharmacology and Experimental Therapeutics 275(2):798–806 (1995).

Deune et al, "Prevention of Ischemia–Reperfusion Injury with a Synthetic Metalloprotein Superoxide Dismutase Mimic, SC52608", Plastic and Reconstructive Surgery 98(4):711–718 (1996).

Lowe et al, "Comparison of the cardiovascular effects of two novel superoxide dismutase mimetics, SC–55858 and SC–54417, in conscious dogs", European Journal of Pharmacoloty 304:81–86 (1996).

Weiss et al, "Manganese–based Superoxide Dismutase Mimetics Inhjibit Neutral Infiltration in Vivo", The Journal of Biological Chemistry 271(42):26149–26156 (1996).

Jin et al, "A new route to water soluble porphyrins: phosphonium and ammonium type cationic porphyrins and self-assembly", Chem. Commun., pp. 1939–1940 (1996).

Pitié et al, "Oxidation at Carbon–1' of DNA Deoxyriboses by the Mn–TMPyP/KHSO5 System Results from a Cytochrome P–450–Type Hydroxylation Reaction", J. Am. Soc. 117:2935–2936 (1995).

Libby et al, "Cationic Porphyrin Derivatives As Inhibitors of Polyamine Catabolism", Biochemical Pharmacology 50(9):1527–1530 (1995).

Ilan et al, "Superoxide Dismuting Activity of an Iron Porphyrin", Inorg. Nucl. Chem. Letters 17(3/4):93–96 (1981).

Solomon et al, "Chemical properties of Water–Soluble Porphyrins. 2. The Reaction of Iron(III) Tetrakis(4–N–methylpyridyl)porphyrin with the Superoxide Radical Dioxygen Couple", J. Phys. Chem. 86:1842–1849 (1982).

Weinraub et al, "Chemical Properties of Water–Soluble Porphyrins. 1. Equilibria between Some Ligands and Iron(III) Tetrakis (4–N–methylpyridyl)porphyrin", J. Phys. Chem. 86:1839–1842 (1982).

Day et al, "A Metalloporphyrin Superoxide Dismutase Mimetic Protects Against Paraquat–Induced Endothelial Cell Injury, in Vitro", The Journal of Pharmacology and Experimental Therapeutics 275(3):1227–1232 (1995).

Kariya et al, "Superoxide Dismutase (SOD) Activity with Fe–chlorin e6–Na and Suppressiion of Malignant Tumor Growth in Rats", Cancer Biotheraphy 10(2):139–145 (1995).

Liochev et al, A Cationic Manganic Porphyrin Inhibits Uptake of Paraquat by *Escherichia Coli*, Archives of Biochemistry and Biophysics 321(1):271–275 (1995).

Ohkawa et al, "Assay for Lipid Peroxides in Animal Tissues by Thiobarbituric Acid Reaction", Analytical Biochemistry 95:351 (1979).

Yue et al, "Carvedilol, a New Vasodilator and Beta Adrenoceptor Antagonist, is an Antioxidant and Free Radical Scavenger", The Journal of Pharmacology and Experimental Therapeutics 263:(1992).

Song et al, "Anti–HIV activities of anionic metalloporphyrins and related compounds", Antiviral Chemistry and Chemotherapy 8(2):85 (1996).

Harriman and Porter, "Photochemistry of Manganese Porphyrins", J. Chem. Soc. 275:1532–1542 (1979).

Bedioui et al, "Metalloporphyrin–Polypyrrole Film Electrode: Characterization and Catalytic Application", J. Electroanal. Chem. 207:87–99 (1986).

Ruoslahti et al, "Arg–Gly–Asp: A Versatile Cell Recognition Signal", Cell 44:517–518 (1986).

Kumar et al, "Radioprotection by Antioxidant Enzymes and Enzyme Mimetics", Pharmac. Ther. 39:301–309 (1988).

Weiss et al, "Evaluation of Activity of Putative Superoxide Dismutase Mimics", The Journal of Biological Chemistry 2638(31):23049–23054 (1993).

Parge et al, "Atomic structures of wild–type and thermostable mutant recombinant human Cu,Zn superoxide dismutase", Proc. Natl. Acad. Sci. USA 89:6109–6113 (1992).

Lappin, "Part III Bioinorganic Studies", Inorganic Reaction Mechanisms 7:334–343 (1981).

Sharma et al, "Synthesis of amphiphilic 5–(4–N–alkylpyridiniumyl)–10,15,20–triphenylporphyrins and their aggregational properties in different solvent systems", Chemical Abstracts vol. 123, No. 1 (1995)—Abstract No. 9222q.

Schneider et al, "Ligand–Porphyrin Complexes: Quantitative Evaluation of Stacking and Ionic Contributions", J. Org. Chem. 59:7464–7472 (1994).

Giraudeau et al, "Substituent Effects in the Electroreduction of Porphyrins and Metalloporphyrins", Journal of the American Chemical Society 101(14):3857–3862 (1979).

Naruta et al, J. Am. Chem. Soc. 113:3595–3596 (1991).

Leondiadis et al, J. Org. Chem. 54:6135–6138 (1989).

Schlözer et al, "Reactivity of Unsubstituted Porphin", German version: Angew. Chem. 87:388 (1975).

Elangovan and Krishnan, "Photophysical properties of porphyrin amphiphiles bearing pyridinium alkyl groups", Chemical Physics Letters 194(1,2):139–146 (1992).

Madakyan et al, "Some metal complexes of meso–tetrakis(3–N–substituted pyridyl)porphyrins and their bioactivity", Arm. Khim. Zh. 42(10):642–646 (1989).

Hambright, Peter, "An acid solvolysis kinetic study of manganese(II)–tetra(2–N–methyipyridyl)porphine", J. Inorg. Chem. 39:1102–1103 (1977).

Vergeldt et al, "Intramolecular Interactions in the Ground and Excited State of Tetrakis(N–methylpyridyl)porphyrins", J. Phys. Chem. 99:4397–4405 (1995).

Louati et al, "Homophophyrines: Effets D'Une Coupure De Conjugaison Cyclique Sur La Reactivite Redox Des Porphyrines", Nouv. J. Chim. 2:163–168 (1978).

* cited by examiner

Fig. 1C

SUBSTITUTED PORPHYRINS

The present application claims benefit of U.S. Provisional Application No. 60/082,881, filed Apr. 24, 1998.

TECHNICAL FIELD

The present invention relates, in general, to a method of modulating physiological and pathological processes and, in particular, to a method of modulating cellular levels of oxidants and thereby processes in which such oxidants are a participant. The invention also relates to compounds and compositions suitable for use in such methods.

BACKGROUND

Oxidants are produced as part of the normal metabolism of all cells but also are an important component of the pathogenesis of many disease processes. Reactive oxygen species, for example, are critical elements of the pathogenesis of diseases of the lung, the central nervous system and skeletal muscle. Oxygen free radicals also play a role in modulating the effects of nitric oxide (NO.). In this context, they contribute to the pathogenesis of vascular disorders, inflammatory diseases and the aging process.

A critical balance of defensive enzymes against oxidants is required to maintain normal cell and organ function. Superoxide dismutases (SODs) are a family of metalloenzymes that catalyze the intra- and extracellular conversion of $O_2^-$ into $H_2O_2$ plus $O_2$, and represent the first line of defense against the detrimental effects of superoxide radicals. Mammals produce three distinct SODs. One is a dimeric copper- and zinc-containing enzyme (CuZn SOD) found in the cytosol of all cells. A second is a tetrameric manganese-containing SOD (Mn SOD) found within mitochondria, and the third is a tetrameric, glycosylated, copper- and zinc-containing enzyme (EC-SOD) found in the extracellular fluids and bound to the extracellular matrix. Several other important antioxidant enzymes are known to exist within cells, including catalase and glutathione peroxidase. While extracellular fluids and the extracellular matrix contain only small amounts of these enzymes, other extracellular antioxidants are also known to be present, including radical scavengers and inhibitors of lipid peroxidation, such as ascorbic acid, uric acid, and α-tocopherol (Halliwell et al, Arch. Biochem. Biophys. 280:1 (1990)).

The present invention relates generally to low molecular weight porphyrin compounds suitable for use in modulating intra- and extracellular processes in which superoxide radicals, or other oxidants such as hydrogen peroxide or peroxynitrite, are a participant. The compounds and methods of the invention find application in various physiologic and pathologic processes in which oxidative stress plays a role.

SUMMARY OF THE INVENTION

The present invention relates to a method of modulating intra- or extracellular levels of oxidants such as superoxide radicals, hydrogen peroxide, peroxynitrite, lipid peroxides, hydroxyl radicals and thiyl radicals. More particularly, the invention relates to a method of modulating normal or pathological processes involving superoxide radicals, hydrogen peroxide, nitric oxide or peroxynitrite using low molecular weight antioxidants, and to methine (ie, meso) substituted porphyrins suitable for use in such a method.

Objects and advantages of the present invention will be clear from the description that follows.

BRIEF DESCRIPTION OF THE DRAWING

FIGS. 1A–1C show the structures of certain compounds of the invention. The SOD activity values were determined using the method of McCord and Fridovich, J. Biol. Chem. 244:6049 (1969). The TBARS values were obtained as follows:

Homogenates

Figure 1A:
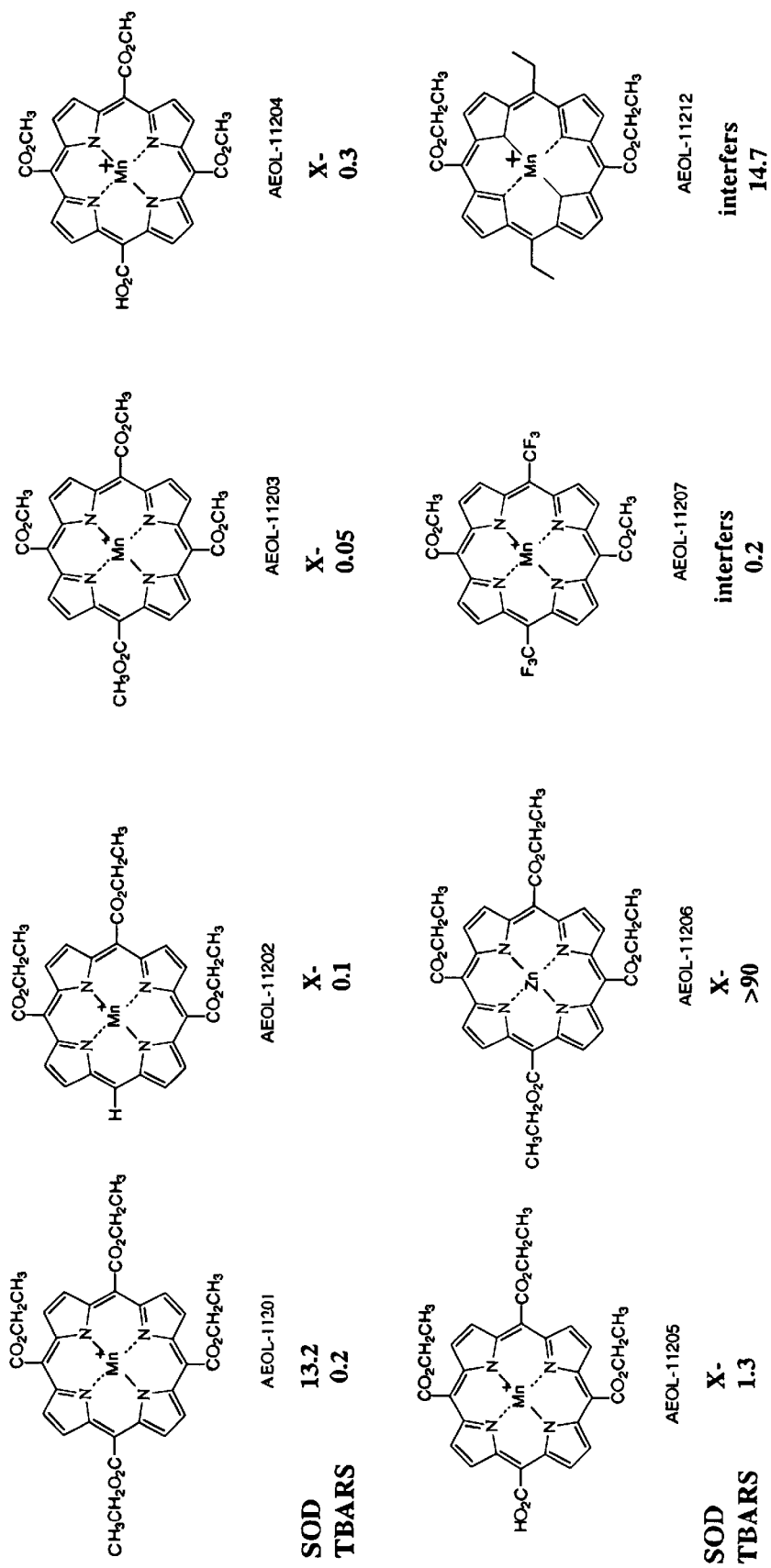

Frozen adult Sprague-Dawley rat brains, livers and mouse lungs (Pel-Freez, Rogers, AR) were homogenized with a polytron (Turrax T25, Germany) in 5 volumes of ice cold 50 mM potassium phosphate at pH 7.4. Homogenate protein concentration was determined with the Coomassie Plus protein assay (Pierce, Rockford, Ill.) using bovine serum albumin as a standard. The homogenate volume was adjusted with buffer to give a final protein concentration of 10 mg/ml and frozen as aliquots at −80° C.

Oxidation of homogenates

Microfuge tubes (1.5 ml) containing 0.2 ml of homogenate (0.2 mg protein) and various concentrations of antioxidant were incubated at 37° C. for 15 minutes. Oxidation of the rat brain homogenate was initiated by the addition of 0.1 ml of a freshly prepared stock anaerobic solution containing ferrous chloride (0.25 mM) and ascorbate (1 mM). Samples were placed in a shaking water bath at 37° C. for 30 minutes (final volume 1 ml). The reactions were stopped by the addition of 0.1 µL of a stock butylated hydroxytoluene (60 mM) solution in ethanol.

Lipid peroxidation measurement

The concentration of thiobarbituric acid reactive species (TBARS) in rat brain homogenates was used as a index of lipid peroxidation. Malondialdehyde standards were obtained by adding 8.2 µL of 1,1,3,3-tetramethoxypropane in 10 ml of 0.01 N HCl and mixing for 10 minutes at room temperature. This stock was further diluted in water to give standards that ranged from 0.25 to 25 µM. Samples or standards (200 µL) were acidified with 200 µL of 0.2 M stock of phosphoric acid in 1.5 ml locking microfuge tubes. The color reaction was initiated by the addition of 25 µL of a stock thiobarbituric acid solution (0.11 M) that was mixed and then placed in a 90° C. heating block for 30 minutes. TBARS were extracted with 0.5 ml of n-butanol by vortexing for 3 minutes and chilling on ice for 1 minute. The samples were then centrifuged at 12,000×g for 3 minutes and a 150 µL aliquot of the n-butanol phase was placed in each well of a 96-well plate and read at 535 nm in a Thermomax platereader (Molecular Devices, Sunnydale, Calif.) at 25° C. Sample absorbances were converted to MDA equivalences (µM) by extrapolation from the MDA standard curve. None of the antioxidants at concentrations employed in these studies affected the reaction of MDA standards with thiobarbituric acid.

Statistical analyses

Data were presented as their means±SE. The inhibitory concentration of antioxidants that decreased the degree of lipid peroxidation by 50% ($IC_{50}$) and respective 95% confidence intervals (CI) were determined by fitting a sigmoidal curve with variable slope to the data (Prizm, GraphPad, San Diego, Calif.). (See also Braughler et al, J. Biol. Chem. 262:10438 (1987); Kikugawa et al, Anal. Biochem. 202:249 (1992).)

DETAILED DESCRIPTION OF THE INVENTION

The present invention relates to methods of protecting against the deleterious effects of oxidants, particularly, superoxide radicals, hydrogen peroxide and peroxynitrite, and to methods of preventing and treating diseases and disorders that involve or result from oxidant stress. The invention also relates methods of modulating biological processes involving oxidants, including superoxide radicals, hydrogen peroxide, nitric oxide and peroxynitrite. The invention further relates to compounds and compositions, including low molecular weight antioxidants (eg mimetics of scavengers of reactive oxygen species, including mimetics of SODs, catalases and peroxidases) and formulations thereof, suitable for use in such methods.

Mimetics of scavengers of reactive oxygen species appropriate for use in the present methods include methine (ie meso) substituted porphines, or pharmaceutically acceptable salts thereof (eg chloride or bromide salts). The invention includes both metal-free and metal-bound porphines. In the case of metal-bound porphines, manganic derivatives of methine (meso) substituted porphines are preferred, however, metals other than manganese such as iron (II or III), copper (I or II), cobalt (II or III), or nickel (I or II), can also be used. It will be appreciated that the metal selected can have various valence states, for example, manganese II, III or V can be used. Zn (II) can also be used even though it does not undergo a valence change and therefore will not directly scavenge superoxide. The choice of the metal can affect selectivity of the oxygen species that is scavenged. Iron-bound porphines, for example, can be used to scavenge NO while manganese-bound porphines scavenge less well.

The mimetics of the present invention are of the Formula I:

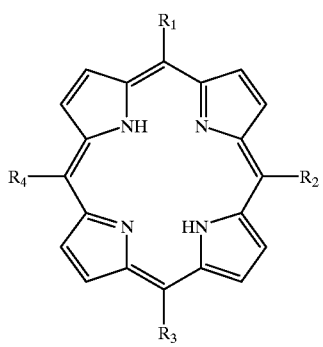

I or pharmaceutically acceptable salt thereof wherein:
$R_1$ and $R_3$ are, independently:
—$CO_2C_{1-4}$ alkyl; or
—$CO_2(CH_2)_nCX_3$, wherein X is halogen and n=1 to 3;
$R_2$ is:
—H
—$C_{1-4}$alkyl
—COOH
—$CO_2C_{1-4}$ alkyl,
—$CO_2(CH_2)_nCX_3$, wherein X is halogen and n=1 to 3,
—$CON(CH_3)_2$, or
—$CX_3$, wherein X is halogen; and
$R_4$ is:
—H,
—$C_{1-4}$alkyl
—COOH,
—$CO_2C_{1-4}$ alkyl,
—$CO_2(CH_2)_nCX_3$, wherein X is halogen and n=1 to 3,
—$CON(CH_3)_2$, or —$CX_3$, wherein X is halogen.

Preferably, $R_1$ and $R_3$ are, independently, —$CO_2C_{1-4}$alkyl (advantageously, —$CO_2C_{1-3}$alkyl) or —$CO_2CH_2CX_3$ (advantageously, where X=F), $R_2$ is —H, —$CO_2C_{1-3}$alkyl, —$CO_2CH_2CX_3$ (advantageously, where X=F), —$CON(CH_3)_2$ or $CX_3$ (advantageously, where X=F) and $R_4$ is —H, —COOH, —$CO_2C_{1-3}$alkyl, —$CON(CH_3)_2$ or —$CX_3$ (advantageously, where X=F).

More preferably, $R_1$ and $R_3$ are, independently, —$CO_2C_{1-3}$alkyl, $R_2$ is —$CO_2C_{1-3}$alkyl, —$CON(CH_3)_2$ or —$CX_3$ (advantageously, where X=F), and $R_4$ is —H, —COOH, —$CO_2C_{1-3}$alkyl, —$CON(CH_3)_2$ or —$CX_3$ (advantageously, where X=F).

Still more preferably, $R_1$ or $R_3$ is —$CO_2CH_3$, —$CO_2CH_2CH_3$, or —$CON(CH_3)_2$, $R_2$ is —$CO_2CH_3$, —$CO_2CH_2CH_3$, or $CX_3$ (advantageously, where X=F), and $R_4$ is —H, —COOH, —$CO_2CH_3$, —$CO_2CH_2CH_3$ or $CX_3$ (advantageously, where X=F).

Even more preferably, $R_1$, $R_2$ and $R_3$ are, independently, —$CO_2CH_3$ or —$CO_2CH_2CH_3$, and $R_4$ is —H, —COOH, —$CO_2CH_3$ or —$CO_2CH_2CH_3$ or —$CO_2CH_2CH_3$.

Most preferably, $R_1$, $R_2$, $R_3$ and $R_4$ are, independently, —$CO_2CH_3$ or —$CO_2CH_2CH_3$.

Figure 1B:
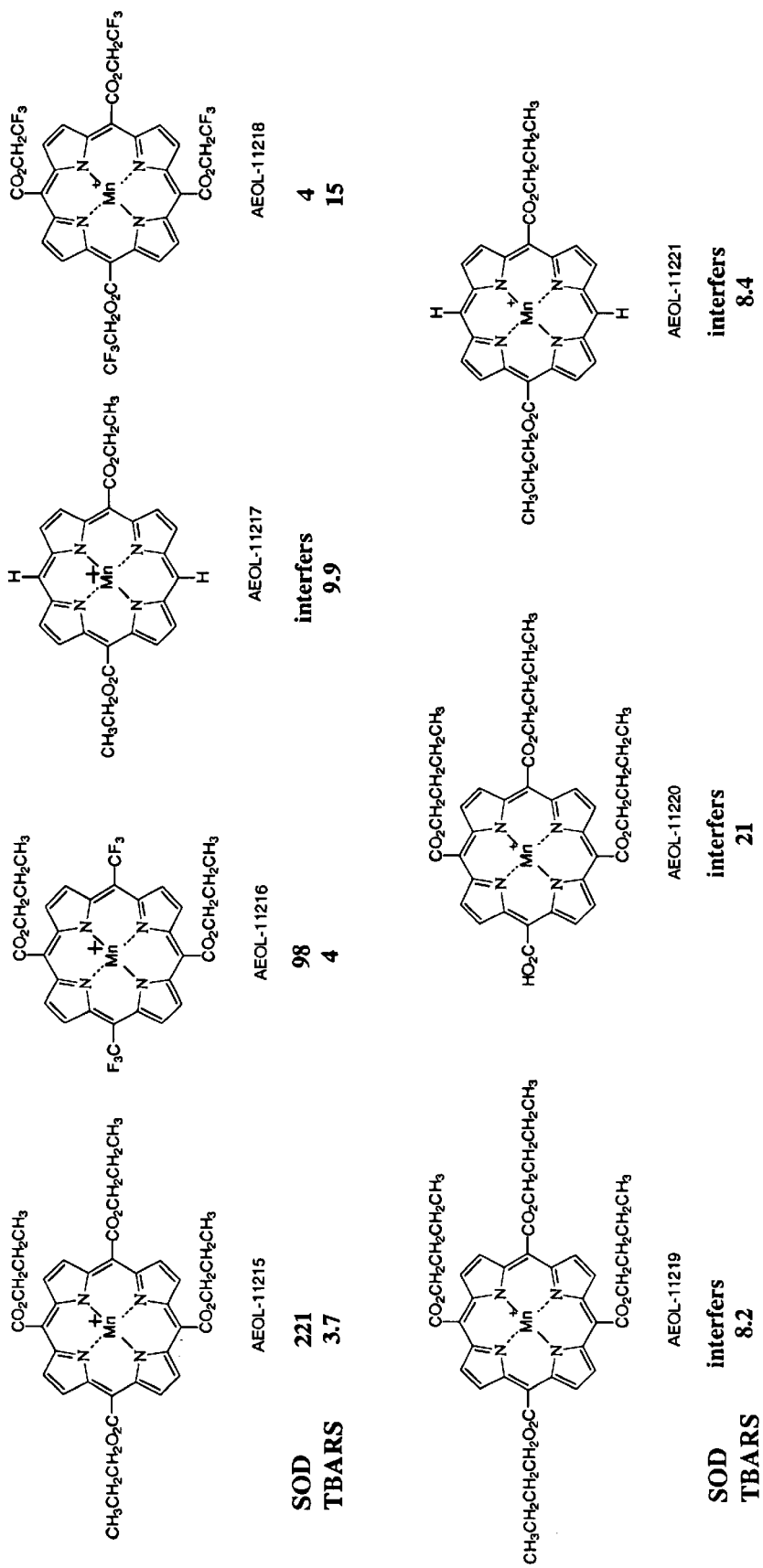
Figure 1C:
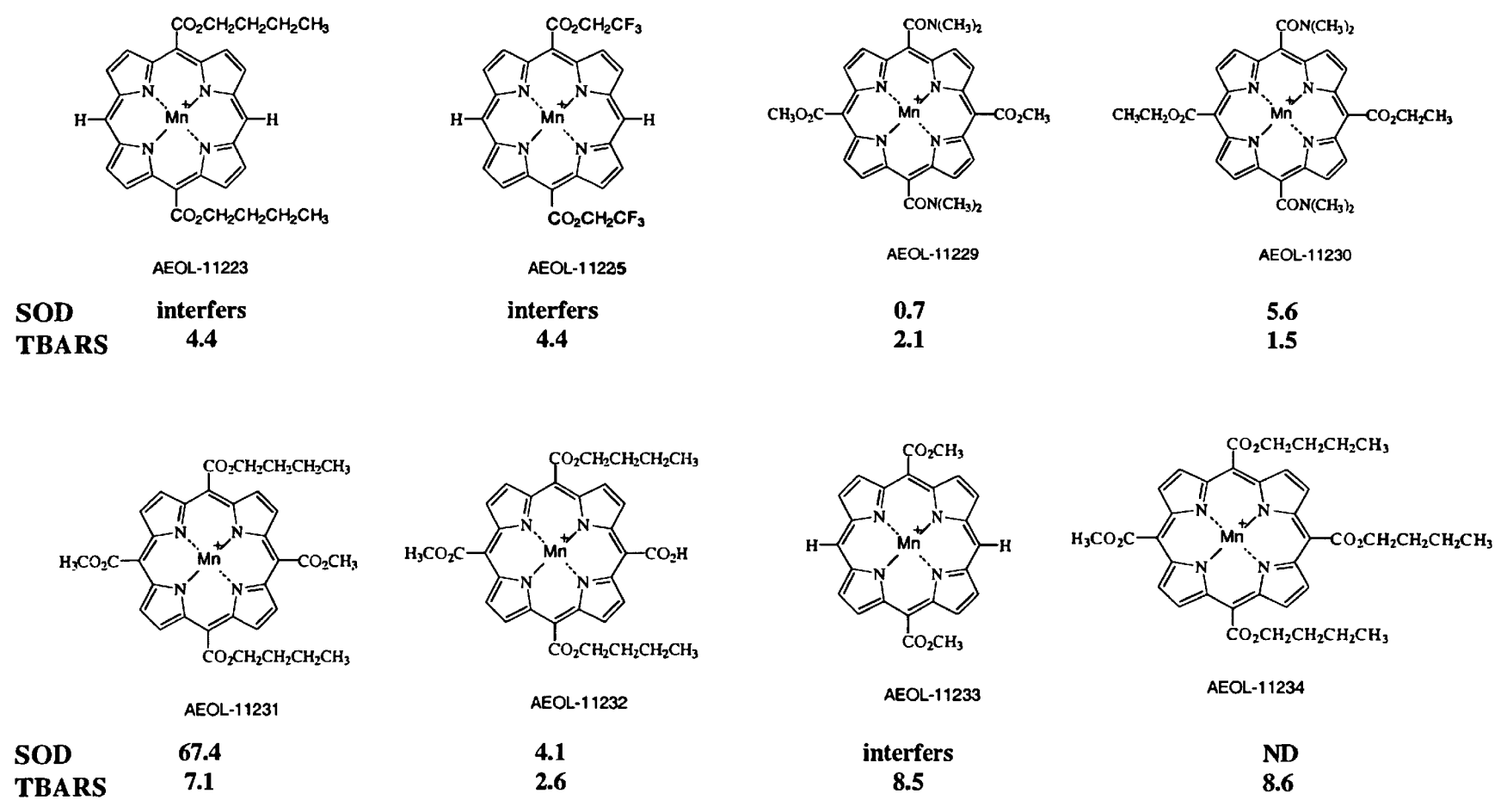

Specific examples of mimetics of the invention are shown in FIG. 1, together with activity data.

In addition to the methine (meso) substituents described above, one or more of the pyrrole rings of the porphyrin of Formula I can be substituted at any or all beta carbons, ie: 2, 3, 7, 8, 12, 13, 17 or 18. Such substituents, designated P, can be hydrogen or an electron withdrawing group, for example, each P can, independently, be a $NO_2$ group, a halogen (eg Cl, Br or F), a nitrile group, a vinyl group, or a formyl group. Such substituents alter the redox potential of the porphyrin and thus enhance its ability to scavenge oxygen radicals. For example, there can be 1, 2, 3, 4, 5, 6, 7, or 8 halogen (eg Br) substituents (preferably, 1–4), the remaining P's advantageously being hydrogen. When P is formyl, it is preferred that there not be more than 2 (on non-adjacent carbons), more preferably, 1, the remaining P's preferably being hydrogen. When P is $NO_2$, it is preferred that there not be more than 4 (on non-adjacent carbons), more preferably, 1 or 2, the remaining P's being hydrogen.

Where isomers are possible, all such isomers of the herein described mimetics are within the scope of the invention.

Mimetics preferred for use in the present methods can be selected by assaying for SOD, catalase and/or peroxidase activity. Minetics can also be screened for their ability to inhibit lipid peroxidation.

SOD activity can be monitored in the presence and absence of EDTA using the method of McCord and Fridovich (J. Biol. Chem. 244:6049 (1969)). The efficacy of a mimetic can also be determined by measuring the effect of the mimetic on the aerobic growth of a SOD null E. coli strain versus a parent strain. Specifically, parental E. coli (AB 1157) and SOD null E. coli. (JI132) can be grown in M9 medium containing 0.2% casamino acids and 0.2% glucose at pH 7.0 and 37° C; growth can be monitored in terms of turbidity followed at 700 nm. This assay can be made more selective for SOD mimetics by omitting the branched chain, aromatic and sulphur-containing amino acids from the medium (glucose minimal medium (M9), plus 5 essential amino acids).

Efficacy of active mimetics can also be assessed by determining their ability to protect mammalian cells against methylviologen (paraquat)-induced toxicity. Specifically, rat L2 cells grown as described below and seeded into 24 well dishes can be pre-incubated with various concentrations of the SOD mimetic and then incubated with a concentration of methylviologen previously shown to produce an $LC_{75}$ in control L2 cells. Efficacy of the mimetic can be correlated with a decrease in the methylviologen-induced LDH release (St. Clair et al, FEBS Lett. 293:199 (1991)).

The efficacy of SOD mimetics can be tested in vivo with mouse and/or rat models using both aerosol administration and parenteral injection. For example, male Balb/c mice can be randomized into 4 groups of 8 mice each to form a standard 2×2 contingency statistical model. Animals can be treated with either paraquat (40 mg/kg, ip) or saline and treated with SOD mimetic or vehicle control. Lung injury can be assessed 48 hours after paraquat treatment by analysis of bronchoalveolar lavage fluid (BALF) damage parameters (LDH, protein and % PMN) as previously described (Hampson et al, Tox. Appl. Pharm. 98:206 (1989); Day et al, J. Pharm. Methods 24:1 (1990)). Lungs from 2 mice of each group can be instillation-fixed with 4% paraformaldehyde and processed for histopathology at the light microscopic level.

Catalase activity can be monitored by measuring absorbance at 240 nm in the presence of hydrogen peroxide (see Beers and Sizer, J. Biol. Chem. 195:133 (1952)) or by measuring oxygen evolution with a Clark oxygen electrode (Del Rio et al, Anal. Biochem. 80:409 (1977)).

Peroxidase activity can be measured spectrophotometrically as previously described by Putter and Becker: Peroxidases. In: Methods of Enzymatic Analysis, H. U. Bergmeyer (ed.), Verlag Chemie, Weinheim, pp. 286–292 (1983). Aconitase activity can be measured as described by Gardner and Fridovich (J. Biol. Chem. 266:19328 (1991)). The selective, reversible and SOD-sensitive inactivation of aconitase by known $O^-_2$ generators can be used as a marker of intracellular $O^-_2$ generation. Thus, suitable mimetics can be selected by assaying for the ability to protect aconitase activity.

The ability of miimetics to inhibit lipid peroxidation can be assessed as described by Ohkawa et al (Anal. Biochem. 95:351 (1979)) and Yue et al (J. Pharmacol. Exp. Ther. 263:92 (1992)). Iron and ascorbate can be used to initiate lipid peroxidation in tissue homogenates and the formation of thiobarbituric acid reactive species (TBARS) measured.

Active mimetics can be tested for toxicity in mammalian cell culture by measuring lactate dehydrogenase (LDH) release. Specifically, rat L2 cells (a lung Type II like cell (Kaighn and Douglas, J. Cell Biol. 59:160a (1973)) can be grown in Ham's F-12 medium with 10% fetal calf serum supplement at pH 7.4 and 37/C; cells can be seeded at equal densities in 24 well culture dishes and grown to approximately 90% confluence; SOD mimetics can be added to the cells at log doses (eg micromolar doses in minimal essential medium (MEM)) and incubated for 24 hours. Toxicity can be assessed by morphology and by measuring the release of the cytosolic injury marker, LDH (eg on a thermokinetic plate reader), as described by Vassault (In: Methods of Enzymatic Analysis, Bergmeyer (ed) pp. 118–26 (1983); oxidation of NADH is measured at 340 nm).

Synthesis of various mimetics suitable for use in the present method can be effected using art-recognized protocols (see, for example Sastry et al, Anal. Chem. 41:857 (1969), Pastemack et al, Biochem. 22:2406 (1983); Richards et al, Inorg. Chem. 35:1940 (1996) and U.S. Appln. No. 08/663,028, particularly the details therein relating to syntheses). Synthesis of a number of mimetics of the invention are set forth in the Examples that follow.

The mimetics of the present invention are suitable for use in a variety of methods. The compounds of Formula I, particularly the metal bound forms (advantageously, the manganese bound forms), are characterized by the ability to inhibit lipid peroxidation. Accordingly, these compounds are preferred for use in the treatment of diseases or disorders associated with elevated levels of lipid peroxidation. The compounds are further preferred for use in the treatment of diseases or disorders mediated by oxidative stress. Inflammation diseases are an example.

The compounds of the invention (advantageously, metal bound forms thereof) can also be used in methods designed to regulate NO. levels by targeting the above-described porphines to strategic locations. NO. is an intercellular signal and, as such, NO. must traverse the extracellular matrix to exert its effects. NO., however, is highly sensitive to inactivation mediated by $O_2^-$ present in the extracellular spaces. The methine (meso) substituted porphyrins of the invention can increase bioavailability of NO. by preventing its degradation by $O_2^-$.

The present invention relates, in a further specific embodiment, to a method of inhibiting production of superoxide radicals. In this embodiment, the mimetics of the invention (particularly,metal bound forms thereof) are used to inhibit oxidases, such as xanthine oxidase, that are responsible for production of superoxide radicals. The ability of a mimetic to protect mammalian cells from xanthine/xanthine oxidase-induced injury can be assessed, for example, by growing rat L2 cells in 24-well dishes. Cells can be pre-incubated with various concentrations of a mimetic and then xanthine oxidase (XO) can be added to the culture along with xanthine (X). The appropriate amount of XO/X used in the study can be pre-determined for each cell line by performing a dose-response curve for injury. X/XO can be used in an amount that produces approximately an $LC_{75}$ in the culture. Efficacy of the mimetic can be correlated with a decrease in XO/X-induced LDH release.

The mimetics of the invention (particularly, metal bound forms thereof) can also be used as catalytic scavengers of reactive oxygen species to protect against ischemia reperfusion injuries associated with myocardial infarction, stroke, acute head trauma, organ reperfusion following transplantation, bowel ischemia, hemorrhagic stock, pulmonary infarction, surgical occlusion of blood flow, and soft tissue injury. The mimetics (particularly, metal bound forms) can further be used to protect against skeletal muscle reperfusion injuries. The mimetics (particularly, metal bound forms) can also be used to protect against damage to the eye due to sunlight (and to the skin) as well as glaucoma, and macular degeneration of the eye. Diseases of the bone are also amenable to treatment with the mimetics. Further, connective tissue disorders associated with defects in collagen synthesis or degradation can be expected to be susceptible to treatment with the present mimetics (particularly, metal bound forms), as should the generalized deficits of aging.

The mimetics of the invention (particularly, metal bound forms) can also be used as catalytic scavengers of reactive oxygen species to increase the very limited storage viability of transplanted hearts, kidneys, skin and other organs and tissues. The invention also provides methods of inhibiting damage due to autoxidation of substances resulting in the formation of $O_2^-$ including food products, pharmaceuticals, stored blood, etc. To effect this end, the mimetics of the invention are added to food products, pharmaceuticals, stored blood and the like, in an amount sufficient to inhibit or prevent oxidation damage and thereby to inhibit or prevent the degradation associated with the autoxidation reactions. (For other uses of the mimetics of the invention, see U.S. Pat. No. 5,227,405). The amount of mimetic to be used in a particular treatment or to be associated with a particular substance can be determined by one skilled in the art.

The mimetics (particularly, metal bound forms) of the invention can further be used to scavenge hydrogen peroxide and thus protect against formation of the highly reactive hydroxyl radical by interfering with Fenton chemistry (Aruoma and Halliwell, Biochem. J. 241:273 (1987); Mello Filho et al, Biochem. J. 218:273 (1984); Rush and Bielski, J. Phys. Chem. 89:5062 (1985)). The mimetics (particularly, metal bound forms) of the invention can also be used to scavenge peroxynitrite, as demonstrated indirectly by inhibition of the oxidation of dihydrorhodamine 123 to rhodamine 123 and directly by accelerating peroxynitrite degradation by stop flow analysis.

Further examples of specific diseases/disorders appropriate for treatment using the mimetics of the present invention, advantageously, metal bound forms, include diseases of the central nervous system (including AIDS dementia, stroke, amyotrophic lateral sclerosis (ALS), Parkinson's disease and Huntington's disease) and diseases of the musculature (including diaphramic diseases (eg respiratory fatigue in emphysema, bronchitis and cystic fibrosis), cardiac fatigue of congestive heart failure, muscle weakness syndromes associated with myopathies, ALS and multiple sclerosis). Many neurologic disorders (including stroke, Huntington's disease, Parkinson's disease, ALS, Alzheimer's and AIDS dementia) are associated with an over stimulation of the major subtype of glutamate receptor, the NMDA (or N-methyl-D-aspartate) subtype. On stimulation of the NMDA receptor, excessive neuronal calcium concentrations contribute to a series of membrane and cytoplasmic events leading to production of oxygen free radicals and nitric oxide (NO.). Interactions between oxygen free radicals and NO. have been shown to contribute to neuronal cell death. Well-established neuronal cortical culture models of NMDA-toxicity have been developed and used as the basis for drug development. In these same systems, the mimetics of the present invention inhibit NMDA induced injury. The formation of $O^-_2$ radicals is an obligate step in the intracellular events culminating in excitotoxic death of cortical neurons and further demonstrate that the mimetics of the invention can be used to scavenge $O^-_2$ radicals and thereby serve as protectants against excitotoxic injury.

The present invention also relates to methods of treating AIDS. The Nf Kappa B promoter is used by the HIV virus for replication. This promoter is used by the HIV virus for replication. This promoter is redox sensitive, therefore, an oxidant can regulate this process. This has been shown previously for two metalloporphyrins distinct from those of the present invention (Song et al, Antiviral Chem. and Chemother. 8:85 (1997)). The invention also relates to methods of treating arritis, systemic hypertension, atherosclerosis, edema, septic shock, pulmonary hypertension, including primary pulmonary hypertension, impotence, infertility, endometriosis, premature uterine contractions, microbial infections, gout and in the treatment of Type II diabetes mellitus. The mimetics of the invention (particularly, metal bound forms) can be used to ameliorate the toxic effects associated with endotoxin, for example, by preserving vascular tone and preventing multi-organ system damage.

As indicated above, inflammations, particularly inflammations of the lung, are amenable to treatment using the present mimetics (articularly, metal bound forms) (note particularly the inflammatory based disorders of asthma, ARDS including oxygen toxicity, pneumonia (especially AIDS-related pneumonia), cystic fibrosis, chronic sinusitis and autoimmune diseases (such as rheumatoid arthitis)). EC-SOD is localized in the interstitial spaces surrounding airways and vasculature smooth muscle cells. EC-SOD and $O_2^-$ mediate the antiinflammatory-proinflammatory balance in the alveolar septum. NO. released by alveolar septal cells acts to suppress inflammation unless it reacts with $O_2^-$ to form $ONOO^-$. By scavenging $O_2^-$, EC-SOD tips the balance in the alveolar septum against inflammation. Significant amounts of $ONOO^-$ will form only when EC-SOD is deficient or when there is greatly increased $O_2^-$ release. Mimetics described herein can be used to protect against destruction caused by hyperoxia.

The invention further relates to methods of treating memory disorders. It is believed that nitric oxide is a neurotransmitter involved in long-term memory potentiation. Using an EC-SOD knocked-out mouse model (Carlsson et al, Proc. Natl. Acad. Sci. USA 92:6264 (1995)), it can be shown that learning impairment correlates with reduced superoxide scavenging in extracellular spaces of the brain. Reduced scavenging results in higher extracellular $O^-_2$ levels. $O^-_2$ is believed to react with nitric oxide thereby preventing or inhibiting nitric oxide-mediated neurotransmission and thus long-term memory potentiation. The mimetics of the invention, particularly, metal bound forms, can be used to treat dementias and memory/learning disorders.

The availability of the mimetics of the invention also makes possible studies of processes mediated by $O_2^-$, hydrogen peroxide, nitric oxide and peroxynitrite.

The miimetics described above, metal bound and metal free forms, can be formulated into pharmaceutical compositions suitable for use in the present methods. Such compositions include the active agent (mimetic) together with a pharmaceutically acceptable carrier, excipient or diluent. The composition can be present in dosage unit form for example, tablets, capsules or suppositories. The composition can also be in the form of a sterile solution suitable for injection or nebulization. Compositions can also be in a form suitable for opthalmic use. The invention also includes compositions formulated for topical administration, such compositions taking the form, for example, of a lotion, cream, gel or ointment. The concentration of active agent to be included in the composition can be selected based on the nature of the agent, the dosage regimen and the result sought.

The dosage of the composition of the invention to be administered can be determined without undue experimentation and will be dependent upon various factors including the nature of the active agent (including whether metal bound or metal free), the route of administration, the patient, and the result sought to be achieved. A suitable dosage of mimetic to be administered IV or topically can be expected to be in the range of about 0.01 to 50 mg/kg/day, preferably, 0.1 to 10 mg/kg/day. For aerosol administration, it is expected that doses will be in the range of 0.001 to 5.0 mg/kg/day, preferably, 0.01 to 1 mg/kg/day. Suitable doses of mimetics will vary, for example, with the mimetic and with the result sought.

Certain aspects of the present invention will be described in greater detail in the non-limiting Examples that follow.

EXAMPLE 1

I. [5,10,15,20-Tetrakis(ethoxycarbonyl)porphyrinato]manganese(III) Chloride (3), [5-Carboxy-10,15,20-tris(ethoxycarbonyl)porphyrinato]manganese(III) Chloride (4) and [5,10,15Tris(ethoxycarbonyl)porphyrinato]manganese(III) Chloride (5)

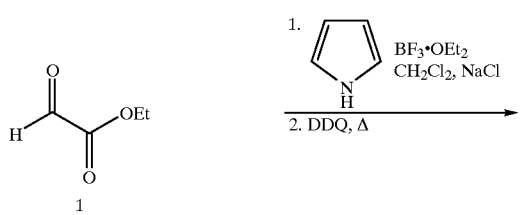
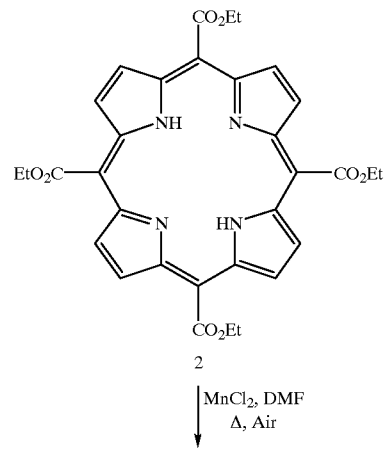
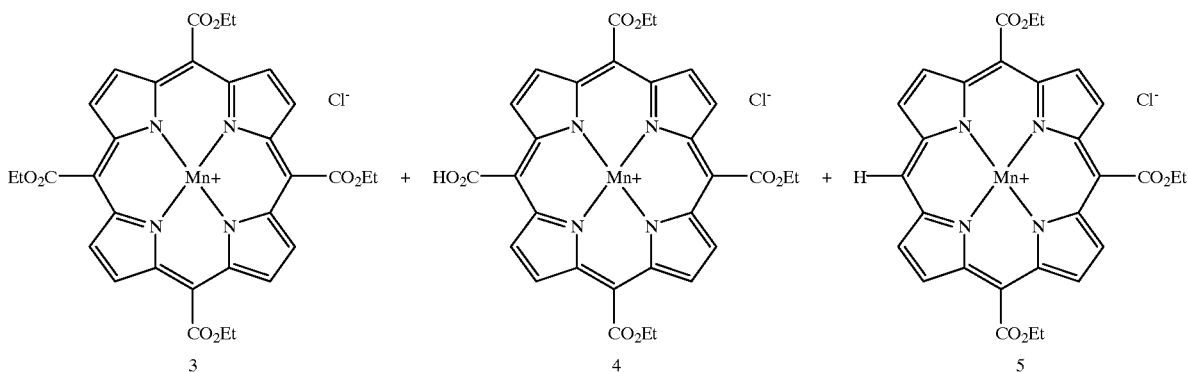

1. 5,10,15,20-Tetrakis(ethoxycarbonyl)porphyrin (2)

In a foil covered, 22 L three-neck round-bottom flask equipped with a mechanical stirrer and a $N_2$ inlet was added consecutively, freshly distilled ethyl glyoxylate (Hook, J. M. *Synth. Commun.* 1984, 14, 83–87) (19.3 g, 189 mmol), $CH_2Cl_2$ (19 L), NaCl (1.1 g, 19 mmol) and pyrrole (13.1 mL, 189 mmol). The reaction mixture was stirred for 5–10 min then $BF_3 \cdot OEt_2$ (7.0 mL, 56 mmol) was added dropwise. After a ring period of 1.25 h at room temperature, 2,3-dichloro-5,6-dicyano-1,4-benzoquinone (DDQ, 32.2 g, 142 mmol) was added. The reaction mixture was stirred for an additional 2 h at room temperature, then clay (Clarion 550, 99 g) was added and the reaction mixture was stirred overnight. Filtration of the heterogeneous mixture through Celite, followed by evaporation of solvents provided a solid mixture which was then adsorbed onto silica gel (24 g). Repeated chromatographic purifications (5 batches; $CH_2Cl_2$ as eluent) on silica gel provided compound 4 (1.7 g; 6%) as a dark solid: $^1$H NMR (300 MHz, CDCl$_3$) δ −3.33 (s, 2H), 1.81 (t, 12H), 5.11 (q, 8H), 9.52 (s, 8H); $^{13}$C NMR (75 MHz, CDCl$_3$) δ14.97, 63.67, 112.43, 131.64, 145.30, 170.68.

2. [5,10,15,20-Tetrakis(ethoxycarbonyl)porphyrinato]manganese(III) Chloride (3)

A solution of 2 (4.43 g, 7.4 mmol) and $MnCl_2$ (4.67 g, 37.1 mmol) in DMF (500 mL) was heated at 145° C. for 1–1.5 h then exposed to a stream of air. The reaction mixture was heated for an additional 2–3 h then allowed to cool to room temperature overnight and under a stream of air. Evaporation of the DME provided a solid mixture which was adsorbed onto silica gel (24 g). Purification by column chromatography (6 batches; gradient elution 0→7% MeOH/$CH_2Cl_2$) provided porphyrin 3 (4.3 g; 84%/) as a dark solid: mp>300° C.; UV-vis $\lambda_{max}$=456 nm, ε=1.08×10$^5$ L/cm-mole; FAB MS m/z=651 $[C_{32}H_{28}MnN_4O_8]^+$.

3. [5-Carboxy-10,15,20-tris(ethoxycarbonyl)porphyrinato]manganese(III) Chloride (4) and [5,10,15-Tris(ethoxycarbonyl)porphyrinato]manganese(III) Chloride (5)

Porphyrins 4 and 5 were also isolated during the chromatographic purification of the previous reaction. Porphyrin 4: mp>300° C.; UV-vis spectroscopy $\lambda_{max}$=460.5 nm, ε=7.8×10$^4$ L/cm-mole; FAB MS m/z=623 $[C_{30}H_{24}MnN_4O_8]^+$. Porphyrin 5: mp>300° C.; UV-vis spectroscopy $\lambda_{max}$=454.5 nm, ε=1.14×10$^5$ L/cm-mole; FAB MS m/z=579 $[C_{29}H_{24}MnN_4O_6]^+$.

EXAMPLE 2

II. [5,10,15,20-Tetrakis(ethoxycarbonyl)porphyrinato]zinc(II) (6)

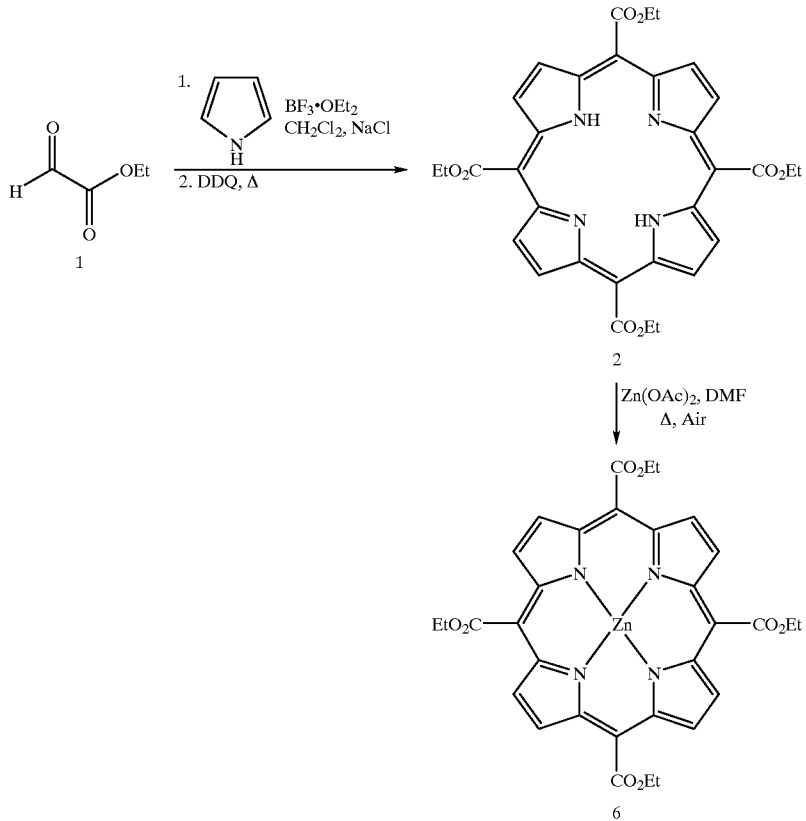

1. [5,10,15,20-Tetrakis(ethoxycarbonyl)porphyrinato]zinc(II) (6)

A solution of 2 (110 mg, 0.18 mmol) and $Zn(OAc)_2$ (403 mg, 18 mmol) in DMF (25 mL) was heated at 145–150° C. for 2 h. The reaction mixture was allowed to cool to room temperature then the DMF was removed by concentration in vacuo. The resulting crude solid mixture was adsorbed onto silica gel (3 g) then purified by column chromatography (gradient elution 0→1% $MeOH/(CH_2Cl_2)$ to provide 6 as a violet solid in 82% yield: mp>300° C., UV-vis spectroscopy $\lambda_{max}$=412.5 nm, $\epsilon$=2.8×10$^5$ L/cm-mole; FAB MS m/z=660 $[C_{32}H_{28}N_4O_8Zn]^+$; $^1$H NMR (300 MHz, DMSO-$d_6$) δ1.79 (t, 12H), 5.09 (q, 8H), 9.56 (s, 8H); $^{13}$C NMR (75 MHz, DMSO-$d_6$) δ14.50, 63.16, 112.57, 132.03, 147.55, 170.67.

EXAMPLE 3

III. [5,10,15,20-Tetrakis(methoxycarbonyl)porphyrinato]manganese(III) Chloride (9) and [5-Carboxy-10,15,20-tris(methoxycarbonyl)porphyrinato]manganese(III) Chloride (10)

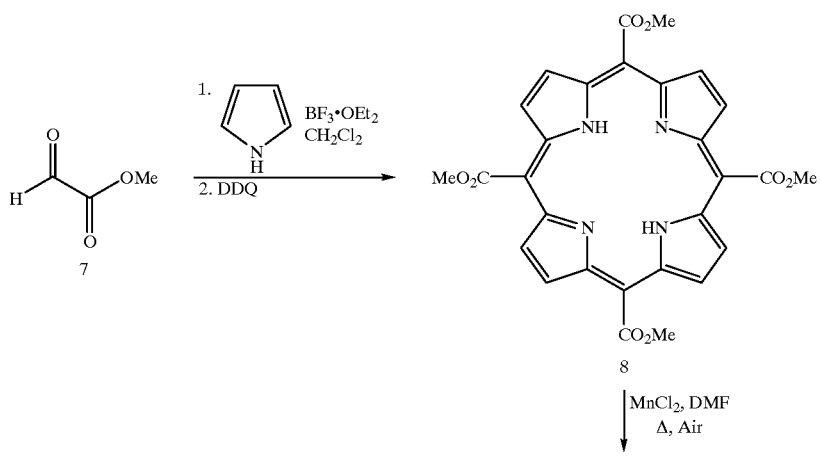

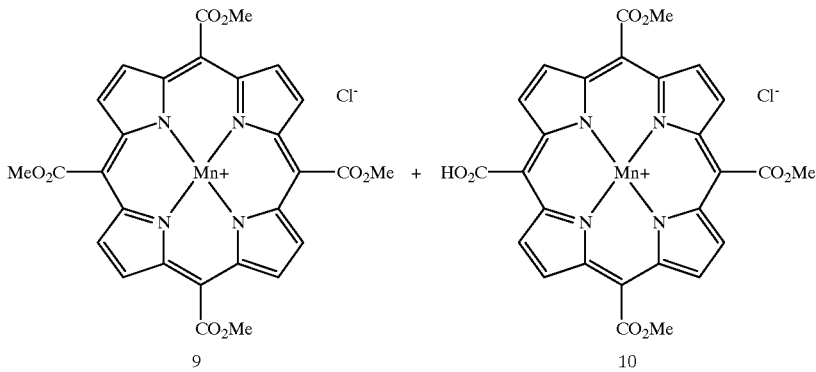

1. 5,10,15,20-Tetrakis(methoxycarbonyl)porphyrin (8)

In a foil covered, 22 L three-neck round-bottomed flask equipped with a mechanical stirrer and a $N_2$ inlet was added sequentially, freshly distilled methyl glyoxylate (7) (Hook, J. M. *Synth. Commun.* 1984, 14, 83–87) (16.5 g, 187 mmol), $CH_2Cl_2$ (19 L), and pyrrole (13.0 mL, 194 mmol). The reaction mixture was stirred for 5–10 min then $BF_3 \cdot OEt_2$ (2.30 mL, 18.7 mmol) was added dropwise. After a stirring period of 1.25 h at room temperature, DDQ (31.9 g, 140.4 mmol) was added. The reaction mixture was stirred for an additional 2.25 h at room temperature, then clay (Clarion 550, 25 g) was added and the suspension was stirred for 2.5 h. Filtration of the reaction mixture through Celite provided, after evaporation of solvents, a crude solid mixture which was adsorbed onto silica gel (15 g). Repeated chromatographic purification (5 batches; $CH_2Cl_2$ as eluent) on silica gel provided porphyrin 8 (1.55 g, 6.1%) as a solid: $^1$H NMR (300 MHz, $CDCl_3$) δ −3.42 (s, 2H), 4.60 (s, 12H), 9.48 (s, 4H); UV-vis $\lambda_{max}$=404.5 nm.

2. [5,10,15,20-Tetrakis(methoxycarbonyl)porphyrinato]manganese(III) Chloride (9)

A solution of 8 (1.11 g, 2.0 mmol) and $MnCl_2$ (1.3 g, 10.3 mmol) in DMF (100 mL) was heated at 145° C. for 1–1.5 h then exposed to a stream of air. The reaction mixture was heated for an additional 2–3 h. The reaction mixture was allowed to cool to room temperature overnight under a stream of air. Evaporation of the DMF provided a solid mixture which was adsorbed onto silica gel (3.5 g). Purification by column chromatography (2 batches; gradient elution 0→10% $MeOH/CH_2Cl_2$) provided porphyrin 9 (760 mg; 59%): mp>300° C.; UV-vis $\lambda_{max}$=455.5 nm, $\epsilon$=8.8×10$^4$ L/cm-mole; FAB MS m/z=595 $[C_{28}H_{20}MnN_4O_8]^+$.

3. [5-Carboxy-10,15,20-tris(methoxycarbonyl)porphyrinato]manganese(III) Chloride (10)

Porphyrin 10 was also isolated by chromatography from the metalation process above: mp>300° C.; UV-vis $\lambda_{max}$=459.5 nm, $\epsilon$=8.5×10$^4$ L/cm-mole; FAB MS m/z=581 $[C_{27}H_{18}MnN_4O_8]^+$.

EXAMPLE 4

IV. [5,15-Bis(methoxycarbonyl)-10,20-bis(trifluoromethyl)porphyrinato]manganese(III) Chloride (15) and [5,15-Bis(trifluoromethyl)-10-carboxy-20-(methoxycarbonyl)porphyriato]manganese(III) Chloride (16)

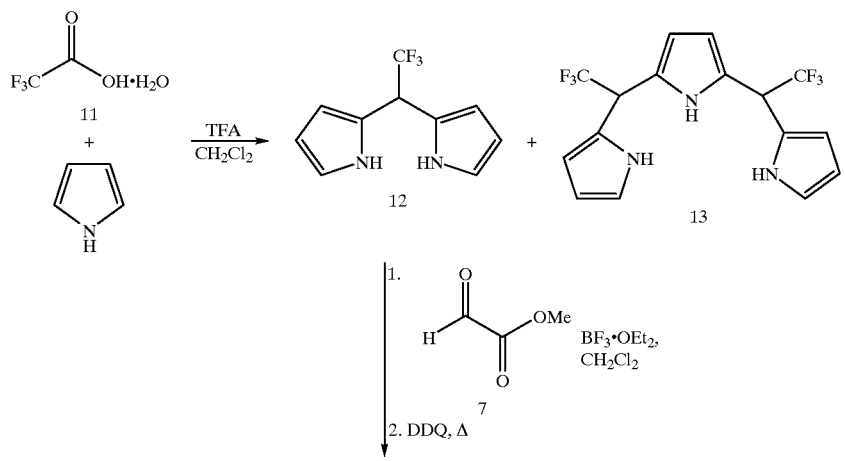

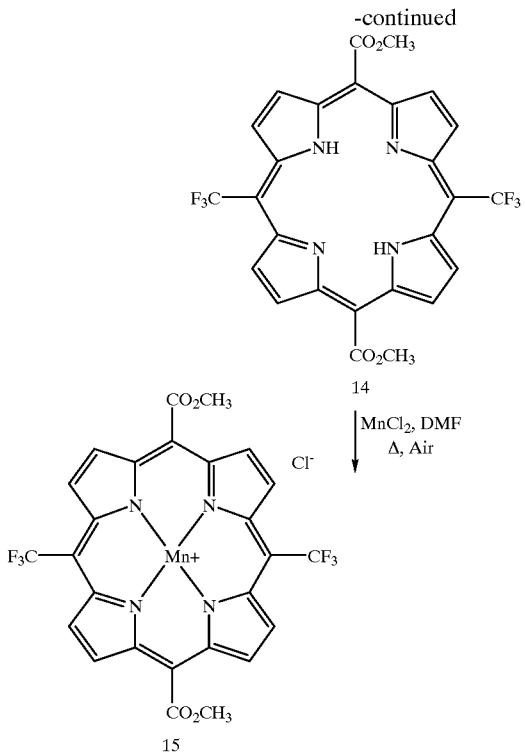

1. meso-(Trifluoromethyl)dipyrromethane (12) (Nishino, N.; Wagner, R. W.; Lindsey, J. S. *J. Org. Chem.* 1996, 61, 7534–7544.)

In a 250 mL round-bottomed flask, equipped with a magnetic stirrer and $N_2$ inlet was placed trifluoracetaldehyde hydrate (11, 6.7 g, 58 mmol), pyrrole (8.0 mL, 116 mmol), and $CH_2Cl_2$ (200 mL). Trifluorocetic acid (4.5 mL, 58 mmol) was then added and the reaction mixture was stirred overnight at room temperature. The reaction mixture was transferred to a separatory funnel, then washed consecutively with $H_2O$ (75 mL) and saturated aqueous $NaHCO_3$ (60 mL). The organic layer was dried ($Na_2SO_4$), filtered, and the solvent removed in vacuo. Column chromatography of the residue provided 12 (2.07 g; 17%) and 13. Dipyrromethane 12: $^1H$ NMR (300 MHz, $CDCl_3$) δ4.85 (q, 1H), 6.19 (m, 4H), 6.77 (m, 2H), 8.09 (broad s, 2H). Tripyrrane 13: $^1H$ NMR (300 MHz, $CDCl_3$) δ4.73 (m, 2H), 6.34 (m, 6H), 6.75 (m, 2H), 7.95 (broad s, 1H), 8.09 (broad s, 2H); DI MS m/z=361 $[C_{16}H_{12}N_3F_6+H]^{30}$.

2. 5,15-Bis(methoxycarbonyl)-10,20-bis(trifluoromethyl)porphyrin (14)

In a foil covered, 500 ml three-neck round-bottomed flask equipped with a magnetic stirrer and a $N_2$ inlet was added consecutively, freshly distilled methyl glyoxylate (Hook, J. M. *Synth. Commun.* 1984, 14, 83–87) (244 mg, 2.77 mmol), dipyrromethane 12 (590 mg, 2.75 mmol) and $CH_2Cl_2$ (280 mL). The reaction mixture was stirred for 5–10 min then $BF_3 \cdot OEt_2$ (112 μL, 0.92 mmol) was added. After stirring period of 2 h at room temperature, DDQ (945 mg 4.1 mmol) was added. The reaction mixture was stirred for an additional 2 h at room temperature, then the solvent was removed in vacuo. The residue was adsorbed onto silica gel (3.8 g) then purified by column chromatography ($CH_2Cl_2$ as eluent) to provide porphyrin 14 (390 mg; 30%): $^1H$ NMR (300 MHz, $CDCl_3$) δ −2.96 (s, 2H), 4.60 (s, 6H), 9.44 (d, 4H), 9.73 (m, 4H).

3. [5,15-Bis(methoxycarbony)-10,20-bis(trafluoromethyl)porphyrinato]manganese(III) Chloride (15)

A solution of 14 (115 mg, 0.20 mmol) and $MnCl_2$ (130 mg, 1.0 mmol) in DMF (30 mL) was heated at 145° C. overnight. The reaction mixture was cooled to room temperature while exposed to a stream of air. Evaporation of DMF provided a solid mixture which was adsorbed onto 3 g silica gel. Purification by column chromatography (gadient elution with 3–10%MeOH/$CH_2Cl_2$) provided porphyrin 15 (117 mg): mp>300° C.; UV-vis $\lambda_{max}$=450 nm, $\epsilon$=9.90×10$^4$ L/cm-mol; FAB MS m/z=615 $[C_{26}H_{14}F_6MnN_4O_4]^+$.

EXAMPLE 5

V. [5,15-Bis(ethoxycarbonyl)porphyrinato]manganese(III) Chloride (21)

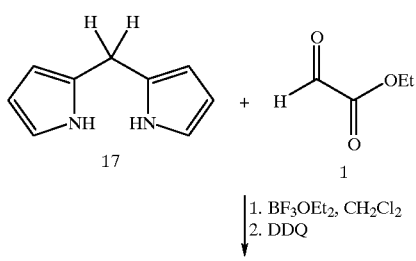

1. $BF_3OEt_2$, $CH_2Cl_2$
2. DDQ

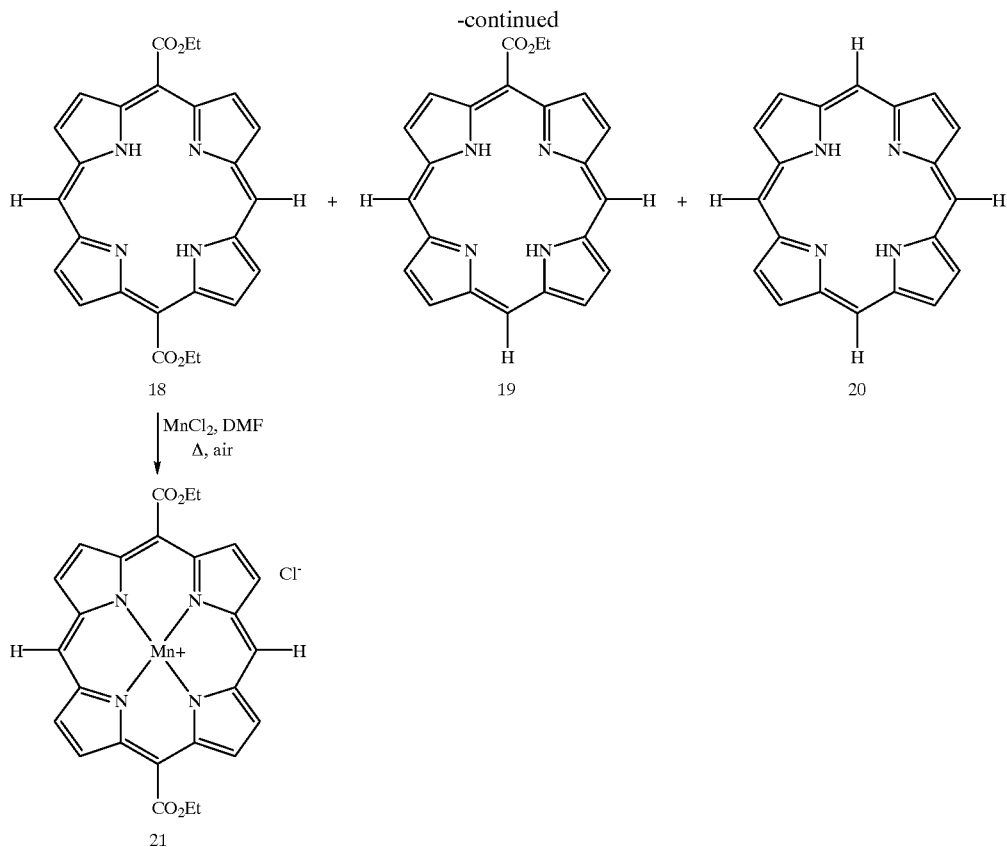

1. 5,15-Bis(ethoxycarbonyl)porphyrin (18)

In a foil covered 250 mL round-bottom flask equipped with a magnetic stir bar and a $N_2$ inlet was added consecutively ethyl glyoxylate (50% in toluene; 310 mg, 1.5 mmol), $CH_2Cl_2$ (150 mL) and dipyrromethane 17 (222 mg, 1.5 mmol) (Chong, et al., *Aust. J. Chem.* 1969, 22, 229.) The reaction mixture was stirred for 5–10 min, then $BF_3 \cdot OEt_2$ (37 μL, 0.3 mmol) was added. After a 30 min stirring period, DDQ (258 mg, 1.14 mmol) was added and the solution was stirred overnight. The crude material was adsorbed onto silica gel (3 g) and was purified by column chromatography (gradient elution with 50→75% $CH_2Cl_2$/hexane) to provide porphyrin 18 (22 mg; 7%): $^1H$ NMR (300 MHz, CDCl3) δ −3.2 (s, 2H), 1.9 (m, 6H), 5.15 (m, 4H), 9.5 (m, 4H), 9.7 (m, 4H) 10.4 (s,2H).

2. 5-(Ethoxycarbonyl)porphyrin (19) and Porphyrin (20)

Porphyrins 19 (10 mg; 2%) and 20 (3 mg; 0.5%), were isolated during chromatographic purification of the previous reaction mixture. For porphyrin 19: $^1H$ NMR (300 MHz, CDCl$_3$) δ −3.74 (s, 2H), 1.87 (t, J=6.9 Hz), 5.16–5.13 (m, 2H), 9.43 (s, 4H), 9.49–9.47 (m, 2H), 9.65 (m, 2H), 10.26 (s, 1H), 10.31 (s, 2H); FAB MS m/z=382 $[C_{23}H_{18}N_4O_2]^+$.

3. [5,15-Bis(ethoxycarbonyl)porphyrinato]manganese(III) Chloride (21)

A solution of porphyrin 18 (22 mg, 0.058 mmol), $MnCl_2$ (55 mg, 0.44 mmol) and anhydrous DMF (8 mL) was heated at 125° C. in a round-bottom flask fitted with a reflux condenser. After 1 h, the reaction mixture was exposed to a stream of air and the solution was stirred overnight. The reaction mixture was allowed to cool to room temperature, then the solvent was evaporated in vacuo. The crude solid material was adsorbed onto silica gel (1.2 g) and purified by column chromatography (gradient elution 0→7% MeOH/$CH_2Cl_2$) to provide 21 (6 mg; 19%) as a dark solid: mp>300° C.; UV-vis $\lambda_{max}$=452.5nm, $\epsilon$=2.48×10$^4$ L/cm-mol; FAB MS m/z=507 $[C_{26}H_{20}MnN_4O_4]^+$.

EXAMPLE 6

VI. [5,10,15,20-Tetrakis(n-propoxycarbonyl)porphyrinato]manganese(III) Chloride (27)

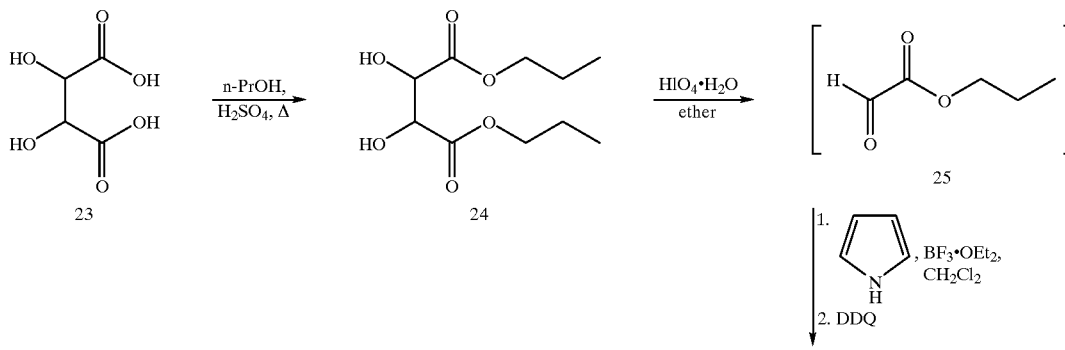

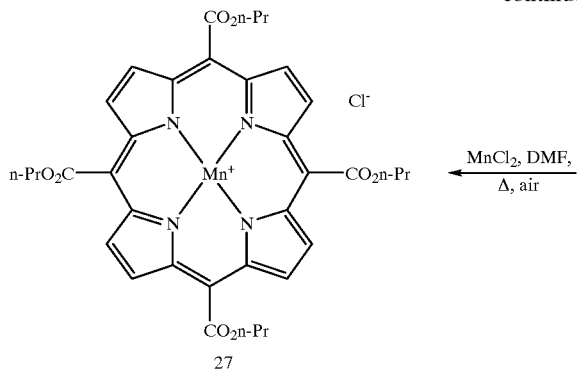

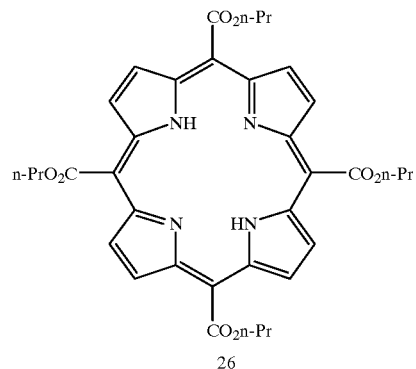

1. Di-n-propyl d-tartrate (24)

d-Tartaric acid (2.56 g, 17.0 mmol), n-propanol (30 mL) and concentrated $H_2SO_4$ (6 mL) were heated under reflux for 3 d. The solution was cooled to room temperature then partitioned between $H_2O$ and $CH_2Cl_2$. The organic layer was washed consecutively with aqueous saturated $NaHCO_3$, $H_2O$, and brine, then dried ($Na_2SO_4$), filtered, and the solvent removed in vacuo. The resulting crude ester 24 (2.6 g, 65%) was used without further purification: $^1H$ NMR (300 MHz, $CDCl_3$) δ1.0 (t, 6H), 1.75 (m 2H), 3.2 (two singlets, 2H), 4.25 (m, 4H), 4.55 (m 2H); DI MS m/z=235 $[C_{10}H_{18}O_6+H]^+$.

2. n-Propyl Glyoxylate (25)

A solution of di-n-propyl d-tartrate (24, 0.73 g, 3.1 mmol) in anhydrous ether (10 mL) was magnetically stirred at 0° C. under dry $N_2$, as periodic acid dihydrate (0.711 g, 3.12 mmol) was added. The resulting solution was stirred for 1 h. Anhydrous $Na_2SO_4$ was added and the resulting milky solution was filtered, and the solvent was evaporated in vacuo to provide 25 as an oil (0.670 g; 93%): CI MS (methane) m/z=117 $[C_5H_8O_3+H]^+$.

3. 5,10,15,20-Tetrakis(n-propoxycarbonyl)porphyrin (26)

To a foil covered, 2 L three-neck round-bottom flask equipped with a magnetic stirrer and a $N_2$ inlet was added consecutively 25 (1.31 g, 11.3 mmol), $CH_2Cl_2$ (1.1 L) and pyrrole (0.78 ml, 11.2 mmol). The reaction mixture was stirred for 5 min, then $BF_3.OEt_2$(416 μL, 3.3 mmol) was added. After a stirring period of 3.5 h, DDQ (1.92 g, 8.5 mmol) was added to the reaction mixture and stirring continued for an additional 2 h at room temperature. Clay (Clarion 550 clay, 6 g) was added and the reaction mixture was allowed to stir overnight. Filtration of the heterogeneous mixture through Celite followed by removal of the solvent in vacuo provided a solid mixture which was adsorbed onto silica gel (2.5 g). Chromatographic purification (gradient elution 66–100% $CH_2Cl_2$/hexanes) provided 27 (130 mg; 7%) as a solid: $^1H$ NMR (300 MHz, $CDCl_3$) δ −3.31 (s, 2H), 1.29 (t, 12H), 2.18 (m, 8H), 5.02 (7, 8H), 9.52 (s, 8H).

4. [5,10,15,2-Tetrakis(n-propoxycarbonyl)porphyrnato] manganese(III) Chloride (27)

A solution of porphyrin 26 (170 mg, 0.260 mmol) and $MnCl_2$ (167 mg, 1.32 mmol) in DNF was heated at 145° C. for 2 h then exposed to a stream of air. The reaction mixture was heated for another 2–3 h then cooled to room temperature overnight under a stream of air. Evaporation of DMF in vacuo provided a solid mixture which was adsorbed onto silica gel (2.6 g). Purification by column chromatography (elution with 2.5% $MeOH/CH_2Cl_2$) provided 27 (170 mg; 88%) as a dark solid: mp>300° C.; UV-vis $\lambda_{max}$=456 nm, $\epsilon = 1.35 \times 10^5$ L/cm·mol; FAB MS m/z=707 $[C_{36}H_{36}MnN_4O_8]^+$.

EXAMPLE 7

VII. [5,15-Bis(n-propoxycarbonyl)-10,20-bis(trifluoromethyl)porphyrinato]manganese(I) Chloride (29)

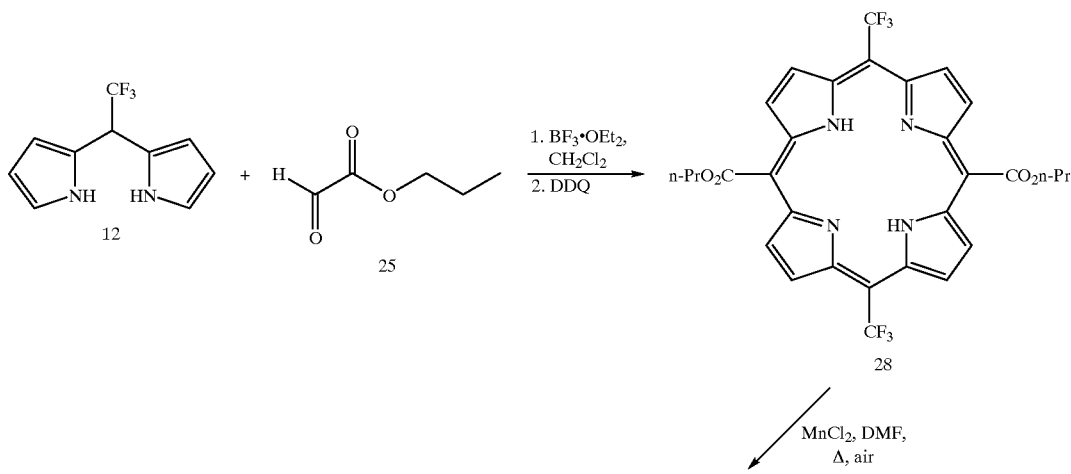

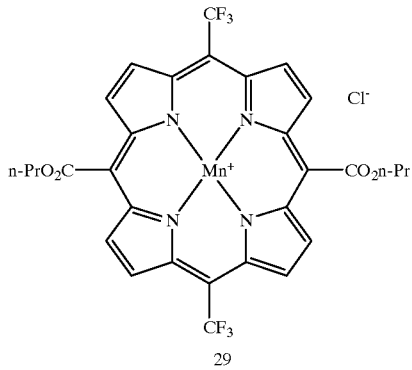

29

1. 5,15-Bis(n-propoxycarbonyl)-10,20-bis(trifluoromethyl)porphyrin (28)

In a foil covered, 250 mL three-neck round-bottomed flask equipped with a magnetic stirrer and a $N_2$ inlet was added consecutively n-propyl glyoxylate (25; 154 mg, 1.3 mmol), dipyrromethane 12 (283 mg, 1.3 mmol) and $CH_2Cl_2$ (130 mL). The reaction mixture was stirred for 5–10 min then $BF_3 \cdot OEt_2$ (32 µL, 0.26 mmol) was added. After 1.5 h at room temperature, DDQ (225 mg, 1.0 mmol) was added. The reaction mixture was stirred for all additional 2 h at room temperature, then treated with clay (Clarion 550, 500 mg). Filtration of the reaction mixture through Celite, followed by evaporation of solvents provided a residue which was absorbed onto silica gel (2.5 g). Column chromatography (elution with 50% $CH_2Cl_2$/hexanes) provided porphyrin 28 (15 mg; 3.7%) as a solid: $^1$H NMR (300 MHz, $CDCl_3$) δ −2.94 (s, 2H), 1.3 (m, 6H), 2.2 (m, 4H), 5.04(t, 4H), 9.46 (d, 4H), 9.74(m, 4H).

2. [5,15-Bis(n-propoxycarbonyl)-10,20-bis(trifluoromethyl)porphyrinato]manganese(III) Chloride (29)

A solution of 28 (15 mg, 0.02 mmol) and $MnCl_2$ (28 mg, 0.22 mmol) in DMF (10 mL) was heated at 145° C. while exposed to a stream of air. After analysis by UV-vis indicated that the reaction was complete, the reaction mixture was cooled to room temperature. Evaporation of DMF provided a solid mixture which was absorbed onto silica gel (1.5 g). Purification by column chromatography (gradient elution with 0→2.5% MeOH/$CH_2Cl_2$) provided porphyrin 28 (15 mg; 87%): UV-vis $\lambda_{max}$=450.5 nm, $\epsilon$=1.10×10$^5$ L/cm-mol; FAB MS m/z=671 $[C_{30}H_{22}F_6MnN_4O_4]^+$.

EXAMPLE 8

VIII. [5,15-Bis(n-propoxycarbonyl)porphyrinato]manganese(III) Chloride (32) and [5-(n-propoxycarbonyl)porphyrinato]manganese(III) Chloride (33)

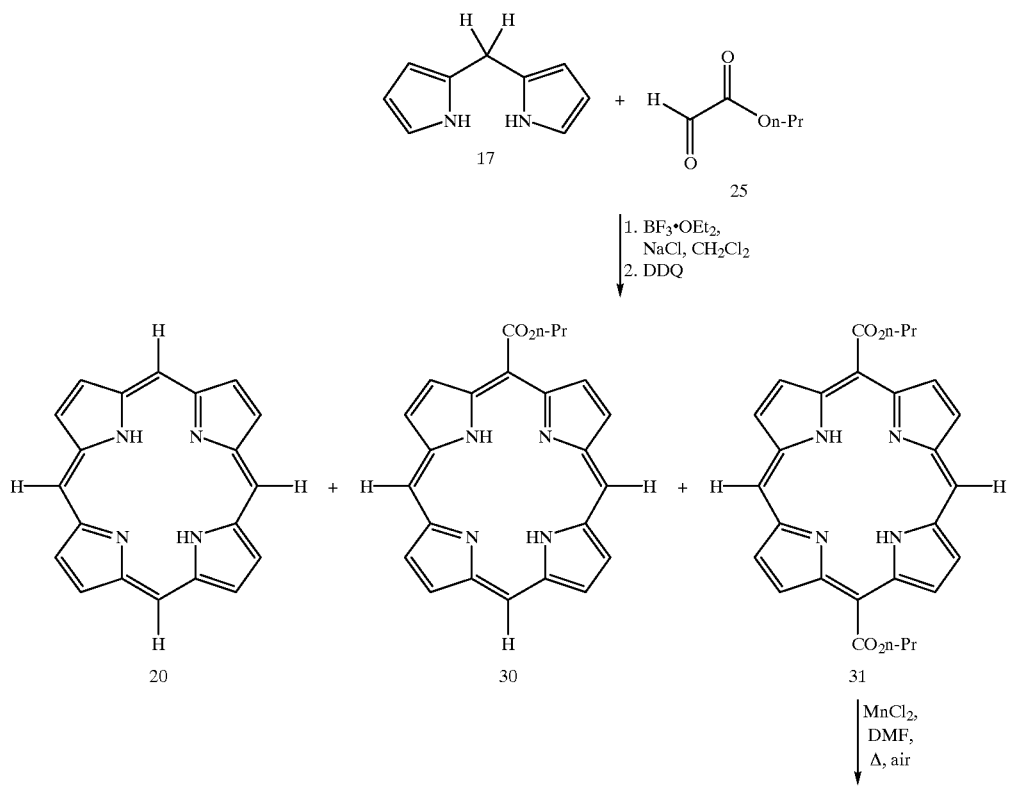

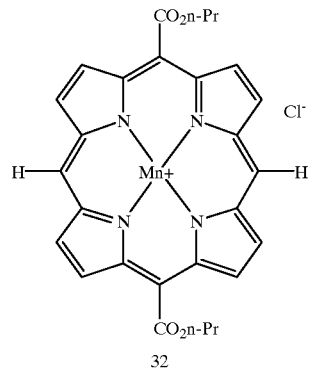

1. 5-(n-Propoxycarbonyl)porphyrin (30) and 5,15-Bis(n-propoxycarbonyl)porphyrin (31)

To a foil covered round-bottom flask equipped with a magnetic stirrer and a $N_2$ inlet was added consecutively dipyrromethade 17 (Chong, et al., Aust. J. Chem. 1969, 22, 229) (0.63 g, 4.3 mmol), $CH_2Cl_2$ (430 mL), n-propyl glyoxylate (25, 0.5 g, 4.3 mmol) and NaCl (23 mg, 0.43 mmol). The reaction mixture was stirred for 5–10 min, then $BF_3 \cdot OEt_2$ (160 μL, 1.3 mmol) was added. After a 65 min stirring period, DDQ (732 mg, 3.23 mmol) was added and the reaction mixture was stirred overnight. Removal of solvents in vacuo provided a crude product which was adsorbed onto silica gel (2 g). Column chromatographic purification (gradient elution with 50%→80% $CH_2Cl_2$/hexane) afforded porphyrin 20, porphyrin 30 (10 mg, 1.2%) and porphyrin 31 (30 mg, 2.9%): For porphyrin 30: $^1$H NMR (300 MHz, $CDCl_3$) δ −3.62 (s, 2H), 1.31 (t, 3H), 2.24 (m, 2H), 5.04 (t, 2H), 9.48 (d, 2H), 9.51 (m, 4H), 9.70 (d, 2H), 10.33 (s, 1H), 10.36 (s, 2H). For porphyrin 31: $^1$H NMR (300 MHz, $CDCl_3$) δ −3.33 (s, 2H), 1.31 (t, 6H), 2.24 (m, 4H), 5.03 (t, 4H), 9.47 (d, 4H), 9.69 (d, 4H), 10.38 (2H).

2. [5,15-Bis(n-propoxycarbonyl)porphyrinato]manganese (III) Chloride (32)

To a magnetically stirred solution of porphyrin 31 (30 mg, 0.062 mmol) in anhydrous DMF (25 mL) was added $MnCl_2$ (39 mg, 0.27 mmol). The reaction flask was fitted with a reflux condenser and the solution was heated to 145° C. for 2 h then exposed to a stream of air. The reaction mixture was heated for an additional 34 h then the solution was allowed to cool to room temperature for 48 h under a stream of air. Evaporation of DMF in vacuo provided a crude product that was adsorbed onto silica gel (2 g). Purification by column chromatography (gradient elution with 5→7.5% MeOH/$CH_2Cl_2$) provided 30 (35 mg; 98%) as a dark solid: mp>300° C.; UV-vis $\lambda_{max}$=452. nm, $\epsilon$=6.10×10$^4$ L/cm-mole; FAB MS m/z=535 $[C_{28}H_{24}MnN_4O_4]^+$.

EXAMPLE 9

IX. [5,10,15,20-Tetrakis(2,2,2-trifluoroethoxycarbonyl)porphyrinato]manganese (III) Chloride (37)

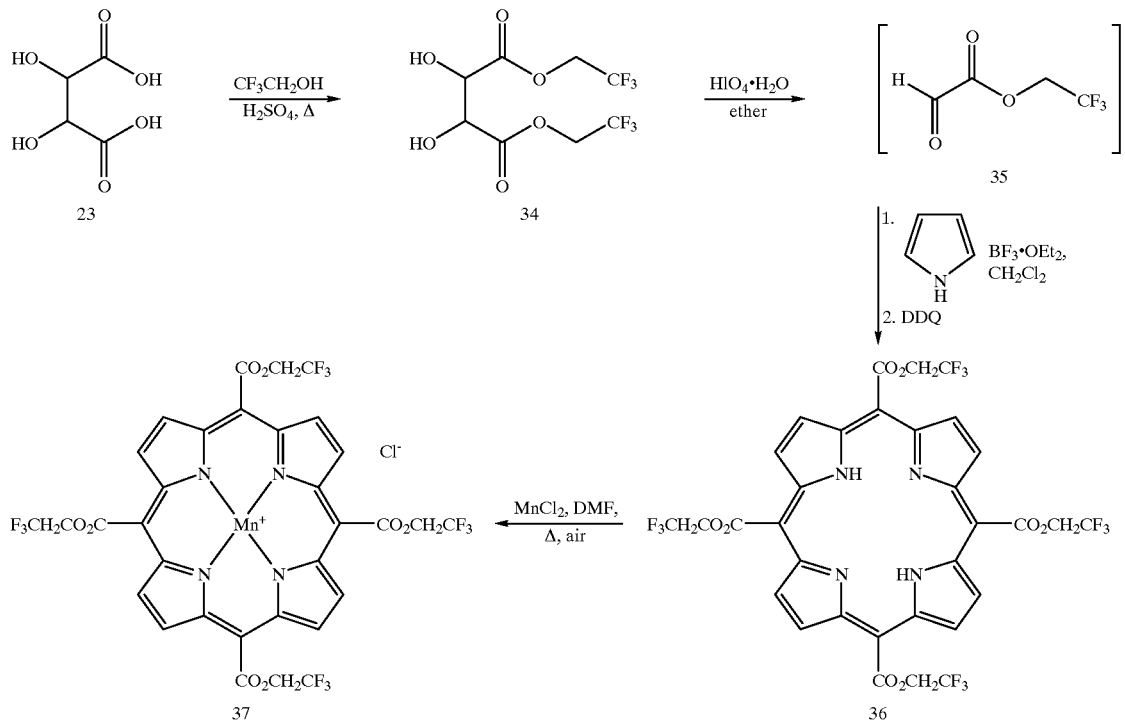

1. Di-(2,2,2-trifluoroethyl) d-tartrate (34)

d-Tartaric acid (23; 25 g, 0.17 mol), trifluoroethanol (200 ml) and $H_2SO_4$ (59 mL) were magnetically stirred and heated under reflux for 22 h. The solution was cooled to room temperature, partitioned between $H_2O$ and $CH_2C_2$. The $H_2O$ layer was extracted with $CH_2Cl_2$ (2×150 mL). The combined organic layers were washed with saturated aqueous $NaHCO_3$, and brine, then filtered through a bed of Celite and evaporated in vacuo. The residue was dissolved in ethyl ether and filtered through a plug of silica. The silica was rinsed with ca. 600 mL. The ether was removed in vacuo and the residue was recrystallized from ether/hexane to yield 34 (17.3; 33%) as white crystals: mp 77–79° C.; $^1H$ NMR (300 MHz, $CDCl_3$) δ3.13 (two singlets, 2H), 4.6 (m, 6H).

2. 2,2,2-Trifluoroethyl glyoxylate (35)

A solution of 34 (1 g, 3.2 mmol) in anhydrous ether (25 mL) was magnetically stirred at 0° C. under dry $N_2$ as periodic acid dihydrate (0.72 g, 3.2 mmol) was added in portions (3×0.24 g) over the course of 1 h. The solution was stirred for an additional 4 h. The reaction solution was decanted, dried ($NaSO_4$), filtered and the solvent removed in vacuo. The material was used immediately and without further purification (0.85 g, 86%).

3. 5,10,15,20-Tetrakis(2,2,2-trifluoroethoxycarbonyl) porphyrin (36)

To a foil covered round-bottomed flask equipped with a magnetic stirrer and $N_2$ inlet was added sequentially 2,2,2-trifluoroethyl glyoxylate 33 (0.85 g, 5.4 mmol), $CH_2Cl_2$ (550 mL) and pyrrole (0.38 mL, 5.4 mmol). The reaction mixture was stirred for 5 min then $BF_3.OEt_2$ (0.20 mL, 1.62 mmol) was added. The reaction mixture was allowed to stir. After a 1.5 h stirring period, DDQ (0.927 g, 4 mmol) was added and the reaction mixture was allowed to stir an additional 30 min. Clay (Clarion 550, 4.17 g) was added and the resulting suspension was stirred for 1 h, then the entire solution was filtered through a bed of Celite. The filtrate was evaporated and adsorbed onto silica gel (2.5 g). Chromatography of the residue on silica (elution with 50–66% $CH_2Cl_2$/hexanes) provided 36 (37 mg; 3.4%) as a solid: $^1H$ NMR (300 MHz, $CDCl_3$) δ −3.6 (s, 2H), 5.5 (q, 8H), 9.5 (s, 8H).

4. [5,10,15,20-Tetrakis(2,2,2-trifuoroethoxycarbonyl) porphyrinato]manganese(III) Chloride (37)

To a round-bottom flask equipped with a magnetic stirrer and a condenser was added porphyrin 36 (36 mg, 0.043 mmol), $MnCl_2$ (27 mg, 0.21 mmol) and DMF (10 ml). The reaction mixture was heated to 140° C. for 2 h, then exposed to a stream of air. After 5 h, an additional amount of $MnCl_2$ (27 mg, 0.21 mmol) was added and the reaction mixture was stirred for 3 d at 100° C. The solvent was removed in vacuo and the residue was adsorbed onto silica gel (1 g). Chromatography on silica gel (gradient elution 0→3% MeOH/$CH_2Cl_2$) provided porphyrin 37 (23 mg; 58%) as a dark solid: FAB MS m/z=867 $[C_{32}H_{16}F_{12}MnN_4O_8]^+$; UV-vis$\lambda_{max}$=453.5 nm, $\epsilon$=7.30×10$^4$ L/cm-mol.

EXAMPLE 10

X. [5,10,15,20-Tetrakis(n-butoxycarbonyl) porphyinato]manganese(III) Chloride (41) and [5Carboxy-10,15,20-tris(n-butoxycarbony) porphyrinato]manganese(III) Chloride (42)

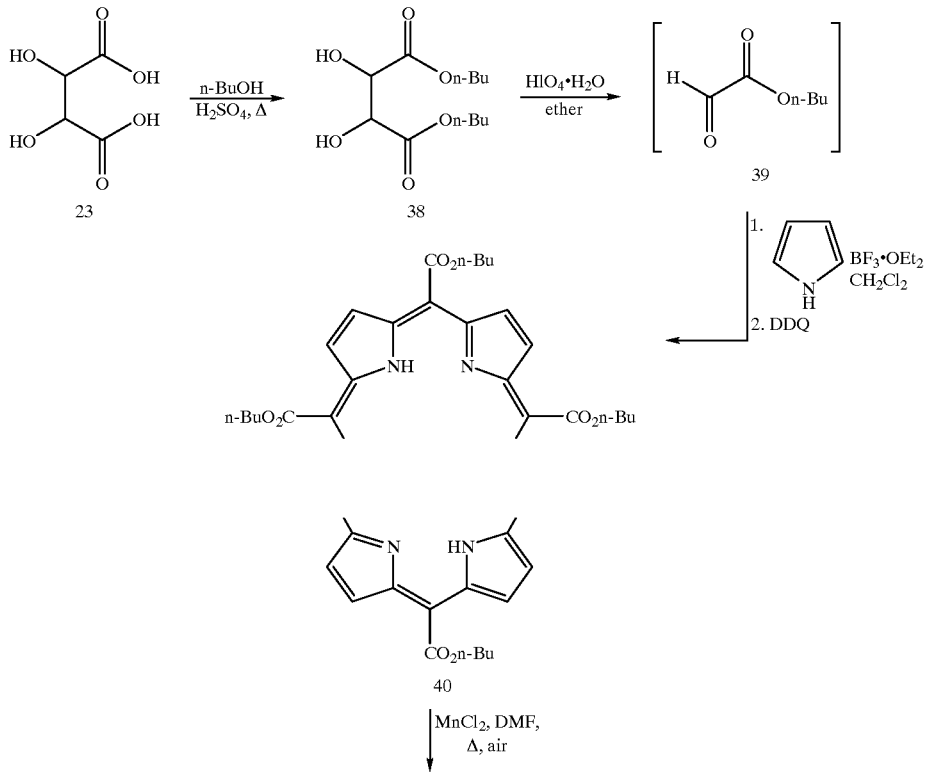

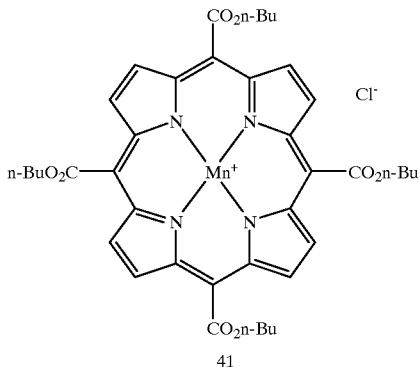 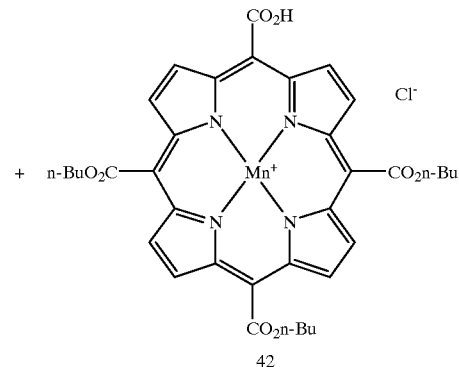

41    42

1. Di-n-butyl d-tartrate (38)

d-Tartaric acid (25 g, 167 mmol), n-butanol (200 mL) and concentrated $H_2SO_4$ (59 mL) were heated under reflux overnight. The solution was cooled to room temperature then partitioned between $H_2O$ and $CH_2Cl_2$. The organic layer was washed with aqueous saturated $NaHCO_3$ then filtered through Celite. The organic solution was then washed with brine, dried ($MgSO_4$), filtered, and the solvent removed in vacuo. The resulting oil was purified by Kugelrohr distillation (bp=100–105° C., 0.06 mm Hg) to yield 38 as a clear light yellow oil: $^1$H NMR (300 MHz, $CDCl_3$) δ 0.9 (t, 6H), 1.4 (m, 4H), 1.65 (m, 4H), 3.2 (m, 2H), 4.35 (m, 4H), 4.5 (m, 2H).

2. n-Butyl Glyoxylate (39)

A solution of tartrate 38 (5 g, 19 mmol) in anhydrous ether (150 mL) was magnetically stirred at 0° C. and under dry $N_2$, as periodic acid dehydrate (4.35 g, 19 mmol) was added over 1 h in portions (3×1.45 g). The resulting solution was stirred for 4 h, decanted from the solid precipitate, dried ($Na_2SO_4$), filtered, and the solvent was removed in vacuo to provide 39 (4.72 g; 96%) as an oil. The crude mixture was used immediately without further purification.

3. 5,10,15,20-Tetrakis(n-butoxycarbonyl)porphyrin (40)

To a foil covered round-bottomed flask equipped with a magnetic stirrer and a $N_2$ inlet was added n-butyl glyoxylate (39, 2.5 g, 19 mmol), $CH_2Cl_2$ (1.9 L), NaCl (0.11 g, 1.9 mmol) and pyrrole (1.33 ml, 19 mmol). The reaction mixture was stirred for 5 min then $BF_3 \cdot OEt_2$ (0.71 ml, 5.7 mmol) was added. After a stirring period of 1 h, DDQ (3.27 g, 14.3 mmol) was added and the reaction mixture was stirred overnight. Clarion 550 clay (15 g) was added and the resulting suspension was allowed to stir for 2–3 h, then filtered through a pad of Celite. The solvent was removed in vacuo and the residue was adsorbed onto silica gel (2 g). Purification by column chromatography (gradient elution with 50→100% $CH_2Cl_2$/hexanes) afforded porphyrin 40 (0.36 g; 11%) as a dark violet solid: $^1$H NMR (300 MHz, $CDCl_3$) δ −3.32 (s, 2H), 1.12 (t, 12H), 1.70 (m, 8H), 2.14 (q, 8H), 5.06 (t, 8H), 9.51(s, 8H).

4. [5,10,15,20-Tetrakis(n-butoxycarbonyl)porphyrinato] manganese(III) Chloride (41) and [5-Carboxy-10,15,20-tris (n-butoxycarbony)porphyrinato]manganese(III) Chloride (42)

A solution of porphyrin 40 (355 mg, 0.50 mmol) and $MnCl_2$ (318 mg, 2.53 mmol) in anhydrous DMF (50 mL) was magnetically stirred and heated to 145° C. for 1 h then exposed to a stream of air for 2 h. The reaction mixture was cooled to room temperature overnight under a stream of air. Evaporation of DMF provided a crude solid mixture which was adsorbed onto silica gel (2 g). Purification by column chromatography (gradient elution with 0–5% MeOH/ $CH_2Cl_2$) provided porphyrins 41 (170 mg) and 42 (10 mg) as solids. For porphyrin 41: mp 200–210° C.; UV-vis $\lambda_{max}$=456.0 nm, $\epsilon$=1.4×10$^5$ L/cm-mol; FAB MS m/z=763 $[C_{40}H_{44}MnN_4O_8]^+$. For porphyrin 42: mp 200–205° C.; UV-vis $\lambda_{max}$=459.5 nm, $\epsilon$=7.2×104 L/cm-mol; FAB MS m/z=707, $[C_{36}H_{36}MnN_4O_8]^+$.

EXAMPLE 11

XI. [5,15-Bis(n-butoxycarbonyl)porphyrinato] manganese(III) Chloride (45)

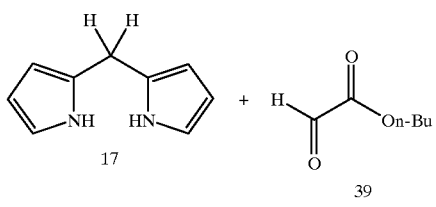

1. $BF_3 \cdot OEt_2$, NaCl, $CH_2Cl_2$
2. DDQ

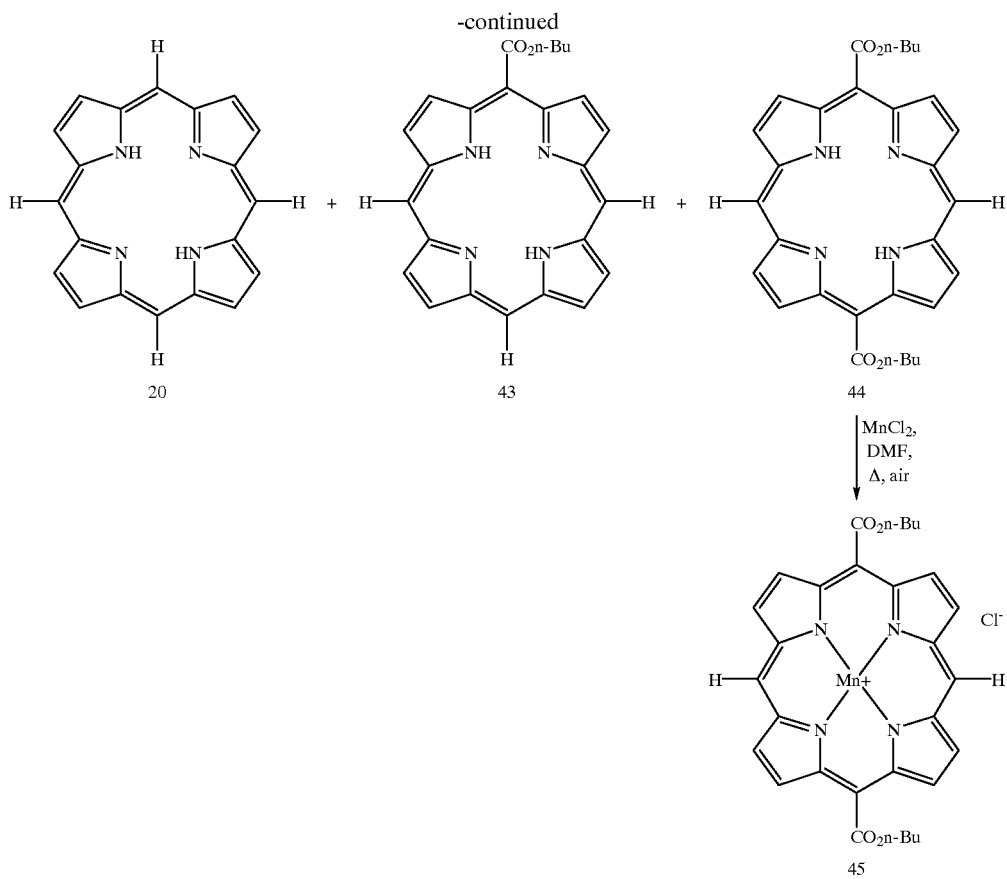

1. 5,15-Bis(n-butoxycarbonyl)porphyrin (44)

To a foil-covered round-bottom flask equipped with a magnetic stirrer and a $N_2$ inlet was added sequentially n-butyl glyoxylate (39, 1.0 g, 7.7 mmol), $CH_2Cl_2$ (390 mL), NaCl (42 mg, 0.77 mmol) and dipyrromethane (1.12 g, 7.7 mmol). The solution was stirred for 5 min, then $BF_3 \cdot OEt_2$ (283 μL, 2.3 mmol) was added and reaction mixture allowed to stir for 30 min. DDQ (1.3 g, 5.8 mmol) was added, and the reaction mixture was stirred for another 30 mm. The solvent was removed in vacuo and the residue was adsorbed onto silica gel (2 g). Purification by column chromatography (gradient elution 50→66% $CH_2Cl_2$/hexane) provided 44 (137 mg; 7%): $^1$H NMR (300 MHz, $CDCl_3$) δ −3.7 (s, 2H), 1.16 (t, 6H), 1.78 (m, 4H), 2.20 (m, 4H), 5.07 (t, 4H), 9.37 (d, 4H), 9.58 (d, 4H), 10.19 (s, 2H).

2. [5,15-Bis(n-butoxycarbonyl)porphyrinato]manganese (III) Chloride (45)

To a round-bottom flask equipped with a magnetic stirrer was added porphyrin 43 (137 mg, 0.27 mmol), $MnCl_2$ (170 mg, 1.3 mmol) and DMF (110 ml). The reaction mixture was heated to 140° C. After a stirring period of 2 h, the reaction was exposed to a stream of air overnight at 110° C. The solvent was removed in vacuo and the residue was adsorbed onto silica gel. Purification by column chromatography on silica (elution with 5% MeOH/$CH_2Cl_2$) provided 45 (65 mg; 43%) as a dark solid: mp>300° C.; UV-vis $\lambda_{max}$=563 nm, $\epsilon = 8.4 \times 10^4$ L/cm-mole; FAB MS m/z=563 $[C_{30}H_{28}MnN_4O_4]^+$.

EXAMPLE 12

XIII. [5,15-Bis(trifluoroethoxycarbonyl) porphyrinato]manganese(III) Chloride (53) and [5-(trifluoroethoxycarbonyl)porphyrinato]manganese (III) Chloride (54)

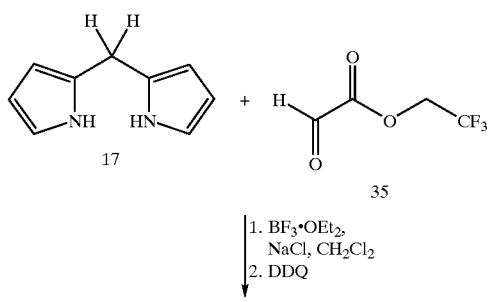

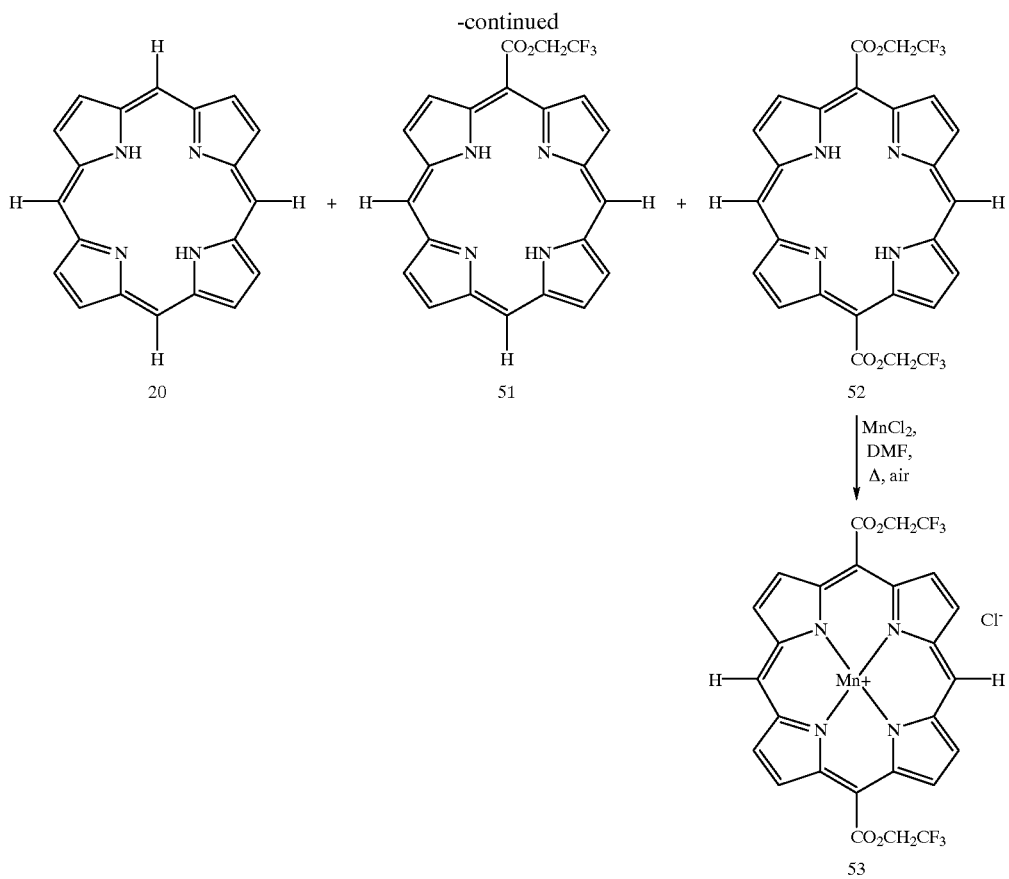

1. 5-Trifluoroethoxycarbonylporphyrin (51) and 5,15-Bis(trifluoroethoxycarbonyl)porphyrin (52)

To a foil covered round-bottom flask equipped with a magnetic stirrer and a $N_2$ inlet was added consecutively dipyrromethane 17 (Chong, et al, *Aust. J. Chem.* 1969, 22, 229) (1.41 g, 9.6 mmol), $CH_2Cl_2$ (1.15 L), trifluoroethyl glyoxylate (35, 1.6 g, 9.6 mmol) and NaCl (53 mg, 0.96 mmol). The reaction mixture was stirred for 5–10 min, then $BF_3 \cdot OEt_2$ (176 µL, 1.43 mmol) was added. After a 30 min stirring period, DDQ (1.63 g, 7.2 mmol) was added and the reaction mixture was stirred overnight. Removal of solvents in vacuo provided a crude product which was adsorbed onto silica gel (2 g). Column chromatographic purification (gradient elution with 50%→80% $CH_2Cl_2$/hexane) afforded porphyrin 20, porphyrin 51 (38 mg) and porphyrin 52 (54 mg). For porphyrin 51: $^1$H NMR (300 MHz, $CDCl_3$) δ −3.58 (s, 2H), 5.43 (q, 2H), 9.45 (m, 4H), 9.51 (d, 2H), 9.70 (d, 2H), 10.30 (s, 1H), 10.35 (s, 2H). For porphyrin 52: $^1$H NMR (300 MHz, $CDCl_3$) δ −3.11 (s, 2H), 5.44 (q, 4H), 9.50 (d, 4H), 9.70 (d, 4H), 10.42 (s, 2H).

2. [5,15-Bis(trifluoroethoxycarbonyl)porphyrinato]manganese(III) Chloride (53)

To a magnetically stirred solution of porphyrin 31 (54 mg, 0.1 mmol) in anhydrous DMF (60 mL) was added $MnCl_2$ (63 m;, 0.5 mmol). The reaction flask was fitted with a reflux condenser and the solution was heated to 145° C. for 2 h then exposed to a stream of air. Additional $MnCl_2$ (63 mg 0.5 mmol) was added for completion of the reaction. The reaction mixture was heated for an additional 3–4 h then the solution was allowed to cool to room temperature for 48 h under a stream of air. Evaporation of DMF in vacuo provided a crude product that was adsorbed onto silica gel (2 g). Purification by column chromatography (gradient elution with 5→7.5% MeOH/$CH_2Cl_2$) provided 53 (45 mg; 72%) as a dark solid: mp>300° C.; UV-vis $\lambda_{max}$=451 nm, $\epsilon$=8×10$^4$ L/cm-mole; FAB MS m/z=615 $[C_{26}H_{14}F_6MnN_4O_4]^+$.

EXAMPLE 13

XV. [5,15-Bis(dimethylamido)-10,20-bis(ethoxycarbonyl)porphyrinato]manganese(III) Chloride (61)

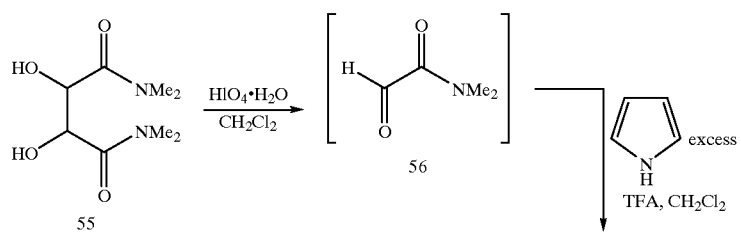

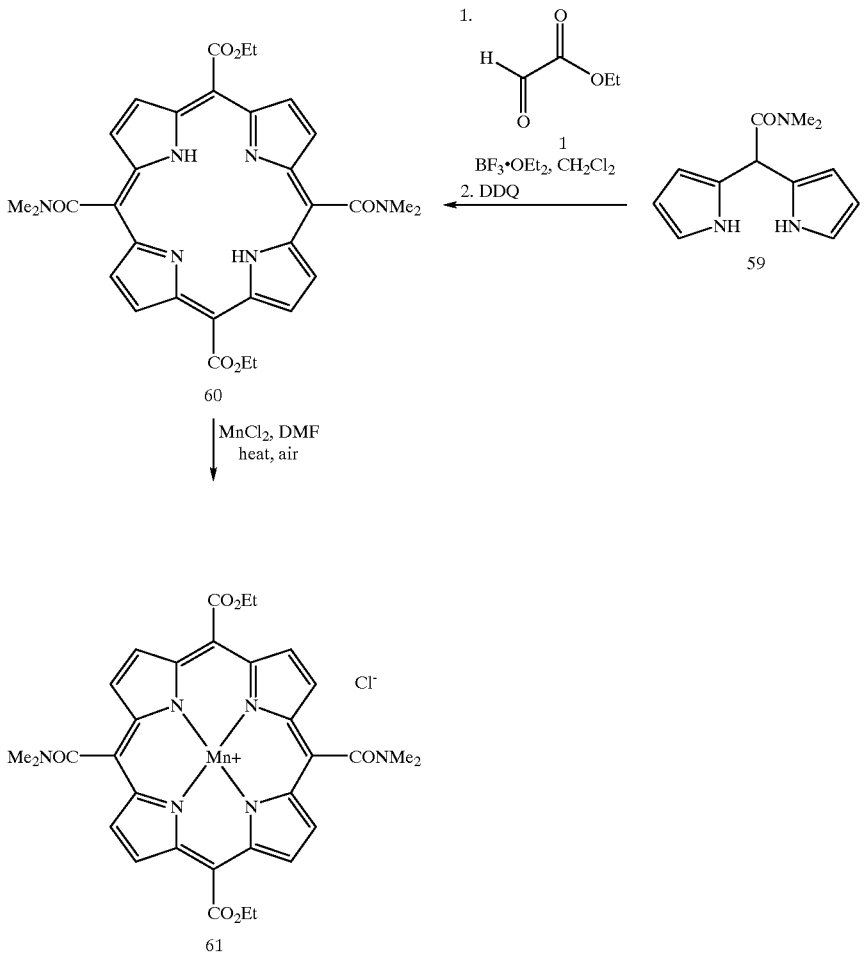

1. meso-(N,N-Dimethylamido)dipyrromethane (59)

In a round-bottom flask equipped with a magnetic stir bar and $N_2$ inlet was placed N,N-dimethyl glyoxamide (56, 2.0 g, 20 mmol), pyrrole (16 mL, 235 mmol) and $CH_2Cl_2$ (40 mL). Trifluoroacetic acid (0.6 mL, 7.8 mmol) was then added. The resulting red-orange solution was stirred overnight at room temperature, transferred into a separatory funnel, diluted with $CH_2Cl_2$, then washed with $H_2O$, saturated aqueous $NaHCO_3$, $H_2O$ and brine. The organic portion was dried ($Na_2SO_4$) and filtered. The solvent was removed in vacuo and the residue was adsorbed onto silica gel (5 g). Purification by chromatography ($SiO_2$, gradient elution with 40% $CH_2Cl_2$/hexanes→3% $CH_3OH/CH_2Cl_2$) afforded dipyrromethane 59 as a light brown solid (1.24 g; 31%): $^1H$ NMR (300 MHz, $CDCl_3$) δ2.99 (s, 3H), 3.18 (s, 3H), 5.41 (s, 1H), 6.03 (broad s, 2H), 6.07 (m, 2H), 6.62 (broad s, 2H), 9.30 (broad s, 2H).

2. 5,15-Bis(dimethylamido)-10,20-bis(ethoxycarbonyl) porphyrin (60)

To a foil covered round-bottom flask equipped with a magnetic stirrer and a $N_2$ inlet was added consecutively dipyrromethane 59 (500 mg, 2.30 mmol), $CH_2Cl_2$(230 mL), ethyl glyoxylate (50% in toluene, 470 mg, 2.30 mmol). The reaction mixture was stirred for 5–10 min, then $BF_3.OEt_2$ (57 μL, 0.46 mmol) was added. After a 45 min stirring period, DDQ (392 mg, 1.73 mmol) was added and the reaction mixture was stirred overnight The solvent was removed in vacuo and the residue was adsorbed onto silica gel (4 g). Repeated purification by column chromatography (gradient elution with 0→3% $CH_3OH/CH_2Cl_2$) afforded porphyrin 60 (7 mg; 1%) as a dark violet solid and as a mixture of atropisomers: $^1H$ NMR (300 MHz, $CDCl_3$) δ −3.2 (s, 2H), 1.8 (t, 6H), 2.8 (m, 6H), 3.8 (s, 6H), 5.1 (m, 4H), 9.3 (d, 4H), 9.5 (d, 4H); FAB MS m/z=597 $[C_{32}H_{32}N_6O_6+H]^+$.

3. [5,15-Bis(dimethylamido)-10,20-bis(ethoxycarbonyl) porphyrinato]manganese(III) Chloride (61)

A solution of 60 (7.0 mg, 0.012 mmol) and $MnCl_2$ (15 mg, 0.12 mmol) in DMF (6 mL) was heated at 145° C. for 1 h then exposed to a stream of air. The reaction mixture was heated for an additional 1.5 h then allowed to cool to room temperature overnight and under a stream of air. Additional $MnCl_2$ (15 mg, 0.12 mmol) was added to the reaction mixture and heated at 145° C. for 1.5 h then exposed to a stream of air for 20 min while hot. The reaction mixture was cooled to room temperature. Evaporation of the DMF provided a solid mixture which was adsorbed onto silica gel (1 g). Purification by column chromatography (10% MeOH/ $CH_2Cl_2$) provided porphyrin 61 as a dark red solid: UV-vis $\lambda_{max}$=458.5 nm; FAB MS m/z=649 $[C_{32}H_{30}MnN_6O_6]^{30}$ .

EXAMPLE 14

XVI. [5,15-Bis(dimethylamido)-10,20bis(methoxycarbonyl)porphyrinato]manganese(III) Chloride (63)

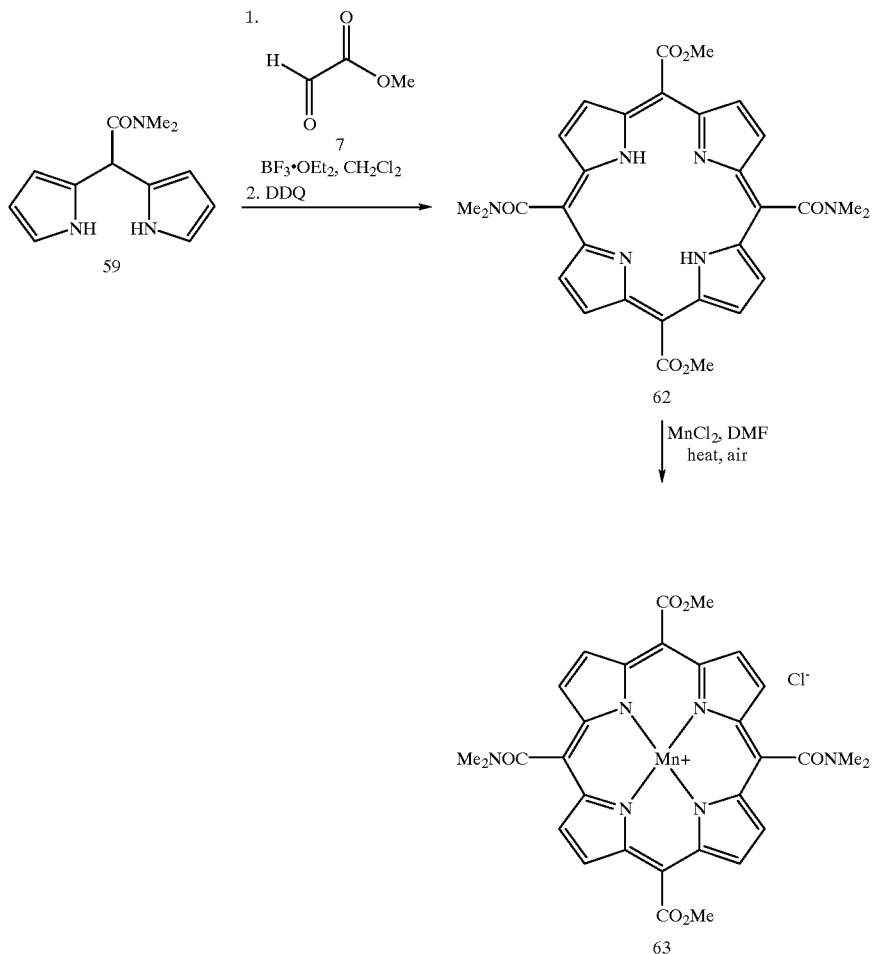

1. 5,15-Bis(dimethylamido)-10,20bis(methoxycarbonyl) porphyrin (62)

To a foil covered round-bottom flask equipped with a magnetic stirrer and a $N_2$ inlet was added consecutively dipyrromethane 59 (915 mg, 4.21 mmol), $CH_2Cl_2$ (400 mL), freshly distilled methyl glyoxylate (370 mg, 4.21 mmol) in $CH_2Cl_2$ (30 mL) and NaCl (25 mg, 0.43 mmol). The reaction mixture was stirred for 5–10 min, then $BF_3 \cdot OEt_2$ (160 µL, 1.26 mmol) was added. After a 30 min stirring period, DDQ (1.43 g, 6.32 mmol) was added and the reaction mixture was stirred overnight. The solvent was removed in vacuo and the residue was adsorbed onto silica gel (4 g). Repeated purification by column chromatography (gradient elution with 0→10% $CH_3OH/CH_2Cl_2$) afforded porphyrin 62 (40 mg; 1.7%) as a dark violet solid mixture of atropisomers: $^1$H NMR (300 MHz, $CDCl_3$) δ −3.1 (s, 2H), 2.71, 2.78 (two singlets, 6H), 3.81 (s, 6H), 4.60 (s, 6H), 9.30 (d, 4H), 9.53 (d, 4H); FAB MS m/z=569 $[C_{30}H_{28}N_6O_6+H]^-$.

2. [5,15-Bis(dimethylamido)-10,20-bis(methoxycarbonyl) porphyrinato]manganese(III) Chloride (63)

A solution of 62 (41 mg, 0.072 mmol) and $MnCl_2$ (181 mg, 1.44 mmol) in DMF (18 mL) was heated at 145° C. for 1.5 h then exposed to a stream of air. The reaction mixture was heated for an additional 1 h then allowed to cool to room temperature overnight under a stream of air. Evaporation of the DMF provided a solid mixture which was adsorbed onto silica gel (1.5 g). Purification by column chromatography (gradient elution with 5→20% $CH_3OH/CH_2Cl_2$) provided a dark red solid. The solid was dissolved in $CH_2Cl_2$ (10 mL) and filtered through a fritted funnel. The residual solid was washed with 2% $CH_3OH/CH_2Cl_2$. The filtrates were combined and the solvent removed in vacuo to afford 63 (10 mg, 21%) as a black solid mixture of atropisomers: mp>300° C.; UV-vis $\lambda_{max}$=458.5 nm, $\epsilon$=3.33×10$^4$ L/cm-mol; FAB MS m/z=621 $[C_{30}H_{26}MnN_6O_6]^+$.

EXAMPLE 15

XVIII. [5,15-Bis(methoxycarbonyl)porphyrinato]manganese(III) Chloride (70) and [5methoxycarbonyl)porphyrinato]manganese(III) Chloride (71)

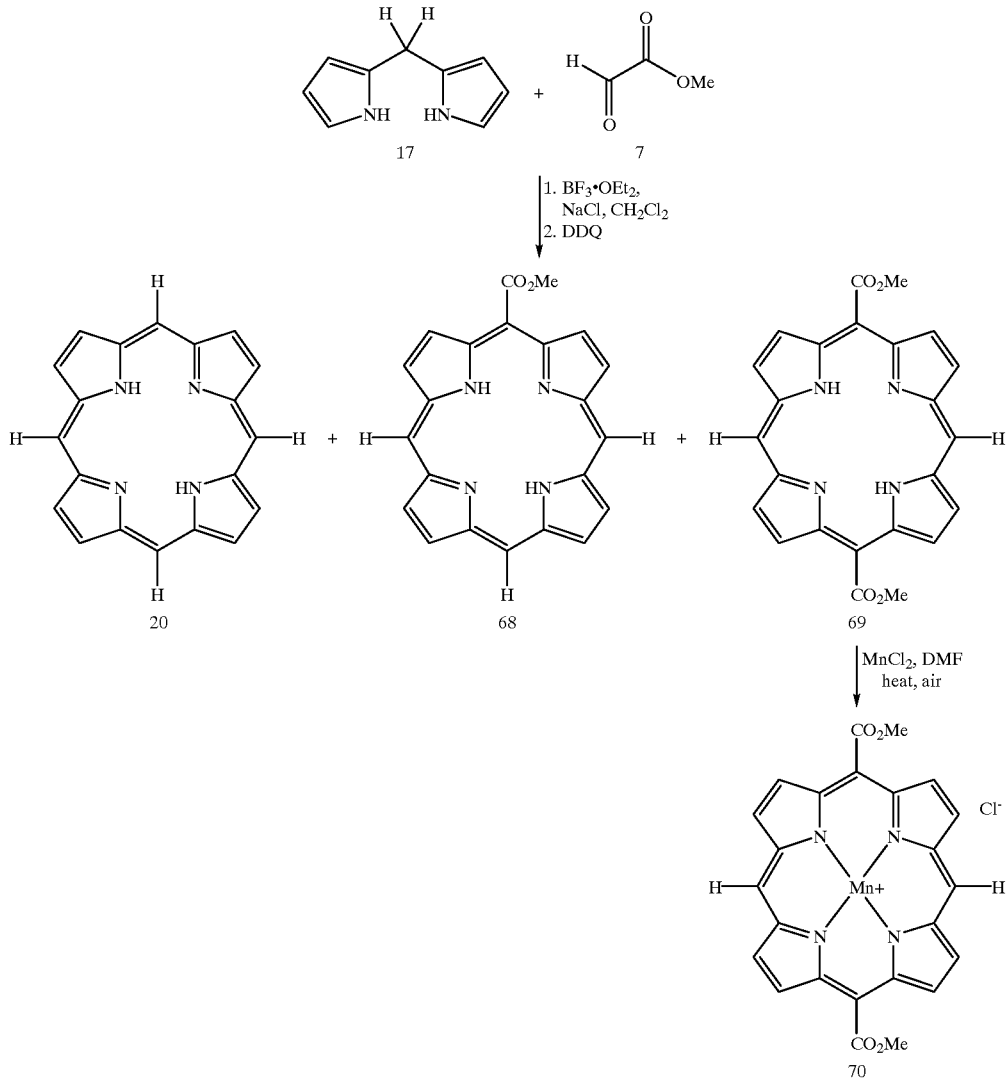

1. 5-(Methoxycarbonyl)porphyrin (68) and 5,15bis(methoxycarbonyl)porphyrin (69)

In a foil covered 3 L round-bottom flask equipped with a magnetic stir bar and a $N_2$ inlet was added consecutively dipyrromethane 17 (2.92 g, 20 mmol), $CH_2Cl_2$ (1900 mL), methyl glyoxylate 7 (1.76 g, 20 mmol) as a solution in $CH_2Cl_2$ (100 mL) and NaCl (118 mg, 2 mmol). The reaction mixture was stirred for 5–10 min, then $BF_3 \cdot OEt_2$ (740 μL, 6.0 mmol) was added. After a 30 min stirring period, DDQ (6.81 g, 30 mmol) was added and the solution was stirred for 2 d. The solvent was removed in vacuo producing, a black tar, which was dissolved in $CH_2Cl_2$/MeOH (99:1) and filtered through a short plug of silica gel. The filtrate was concentrated, then adsorbed onto silica grel (1 g), and purified by column chromatography (gradient elution with 33% hexanes/$CH_2Cl_2 \rightarrow 100\%$ $CH_2Cl_2$) to provide porphyins 20, 68 (30 mg, 0.7%), and 69 (61 mg; 1.4%). Porphyrin 68: $^1$H NMR (300 MHz, CDCl$_3$) δ −3.6 (s, 2H), 4.6 (s, 3H), 9.49–9.53 (m, 6H), 9.7 (d, 2H), 10.3–10.5 (m, 3H). Porphyrin 69: $^1$H NMR (300 MHz, CDCl$_3$) δ −3.2 (s, 2H), 4.6 (s, 6H), 9.5 (d, 4H), 9.7 (d, 2H), 10.4 (s, 2H).

2. [5,15-Bis(methoxycarbonyl)porphyrinato]manganese(III) Chloride (70)

To a magnetically stirred solution of porphyrin 69 (61 mg, 0.142 mmol) in anhydrous DMF (70 mL) was added MnCl$_2$ (90 mg, 0.71 mmol). The reaction mixture was heated at 150° C. for 2 h then exposed to a stream of air. The reaction solution was heated for an additional 2–3 h, then the solution was allowed to cool to room temperature overnight under a stream of air. Then the reaction mixture was heated again to 150° C. and stirred for another 4 h. Evaporation of DMF in vacuo provided a solid mixture which was adsorbed onto silica gel (1 g). Purification by column chromatography (5% MeOH/$CH_2Cl_2$) provided compound 70 (25 mg; 34%) as a dark solid: mp>300° C.; UV-vis $\lambda_{max}$=452.0 nm, ε=4.40× 10$^4$ L/cm-mol; FAB MS m/z=479 $[C_{24}H_{16}MnN_4O_4]^+$.

EXAMPLE 16
XX. [5,15-Bis(n-butoxycarbonyl)-10,20-bis(methoxycarbonyl)porphyrinato]manganese(III) Chloride (79), [10,20-Bis(n-butoxycarbonyl)-5carboxy-15-(methoxycarbonyl)porphyrinato]manganese(III) Chloride (80), [5,15-Bis(n-butoxycarbonyl)-10-(methoxycarbonyl)porphyrinato]manganese(III) Chloride (81) and [5methoxycarbonyl-10,15,20-tri(butoxycarbonyl)porphyrinato]manganese(III) Chloride (82)
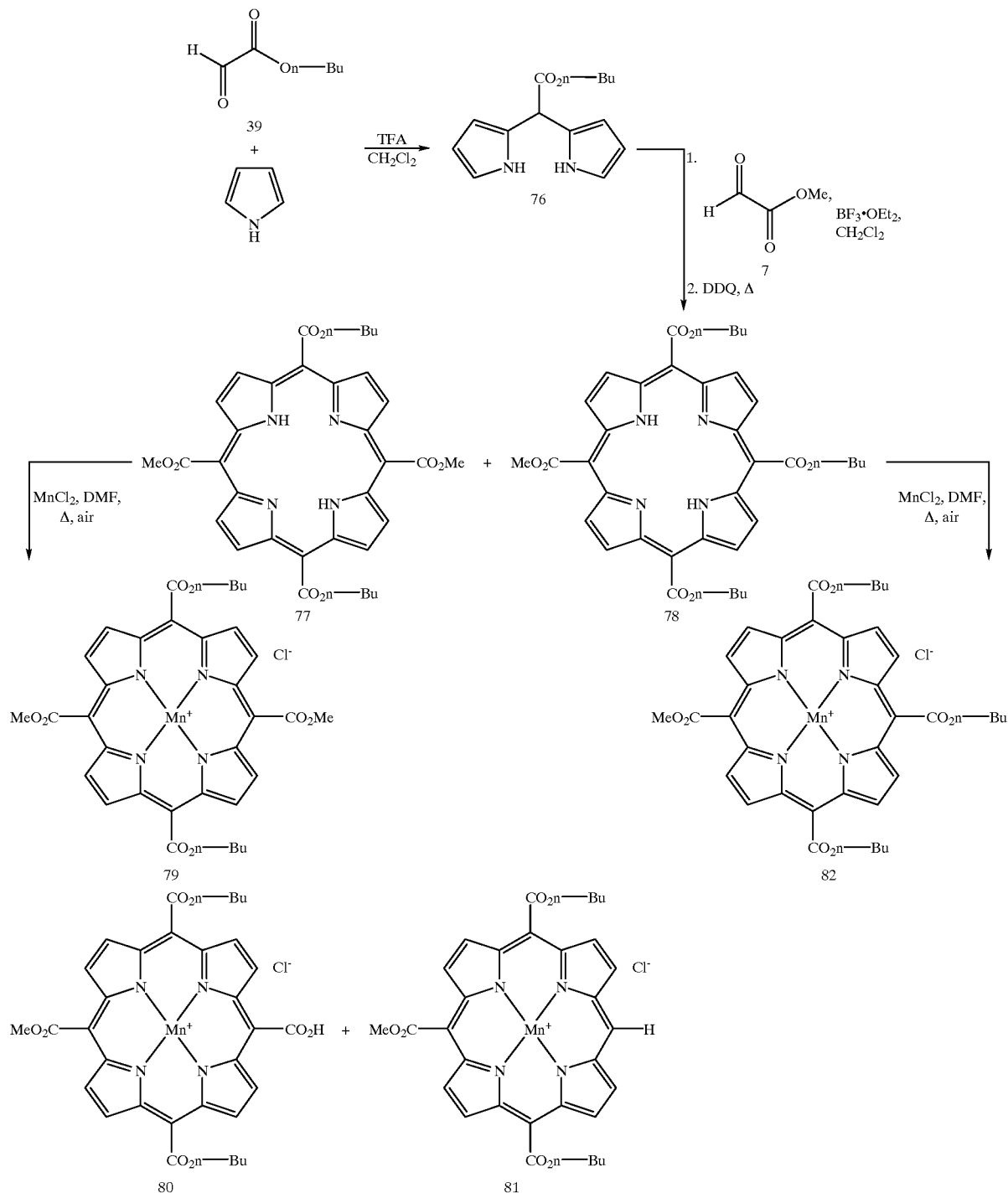

1. (n-Butoxycarbonyl)dipyrromethane (76)

A solution of n-butyl glyoxylate (39) (3.85 g, 29.6 mmol) in CH$_2$Cl$_2$ (100 ml) was magnetically stirred under N$_2$, in a flask covered with foil. Pyrrole (24.6 ml, 355 mmol) was added and the reaction mixture was allowed to stir overnight. A black product mixture was obtained after evaporation of solvents. This material was filtered through a plug of silica using, CH$_{hd\ 2}$Cl$_2$ as eluent. Column chromatography of the residue on silica gel (eluent: 1:1 hexane:CH$_2$Cl$_2$) provided pure dipyromethane 76 (1.04 g, 14%).

2. 5,15-Bis(n-butoxycarbonyl)-10,20-bis(methoxycarbonyl) porphyrin (77) and 5-Methoxycarbonyl-10,15,20-Tris(n-butoxycarbonyl)porphyrin (78)

In a foil covered, 500 mL three-neck round-bottomed flask equipped with a magnetic stirrer and a N$_2$ inlet was added consecutively methyl glyoxylate (376 mg, 4.27 mmol), dipyromethane 39 (1.04 g, 4.23 mmol), NaCl (27 mg, 0.46 mmol), and CH$_2$Cl$_2$ (420 mL). The reaction mixture was stirred for 5–10 min then BF$_3$.OEt$_2$ (155 μL, 1.26 mmol) was added. After a stirring period of 30 min at room temperature, DDQ (1.43 g, 6.3 mmol) was added. The reaction mixture was stirred for an additional 2 h at room temperature, then the solvent was removed in vacuo. The residue was purified by repeated chromatographic purifications to provide porphyrins 77 (75 ma) and 78 (20 mg). Porphyrin 77: $^1$H NMR (300 MHz, CDCl$_3$) δ –3.41 (s, 2H), 1.11 (t, 6H), 1.69 (m, 4H), 2.12 (m, 4H), 4.59 (s, 6H), 5.05 (t, 4H), 9.49 (s, 8H). Porphyrin 78: $^1$H NMR (300 MHz, CDCl$_3$) δ –3.34 (s, 2H), 1.11 (7,9H), 1.70 (m, 6H), 2.13 (m, 6H), 4.60 (s, 3H), 5.05 (t, 6H), 9.51 (s, 8H).

3. [5,15-Bis(n-butoxycarbonyl)-10,20-bis(methoxycarbonyl)porphyrinato]manganese(III) Chloride (79), [10,20-Bis(n-butoxycarbonyl)-5-carboxy-15-(methoxycarbonyl) porphyrinato]manganese(III) Chloride (80), [5,15-Bis(n-butoxycarbonyl)-10-(methoxycarbonyl)porphyrinato] manganese(III) Chloride (81)

A solution of 77 (75 mg, 0.12 mmol) and NInCl$_2$ (163 mg, 1.30 mmol) in DMF (35 mL) was heated at 145° C. for 2 h. The reaction mixture was then exposed to a stream of air as it cooled to room temperature. Evaporation of DMF provided a solid mixture which was adsorbed onto 2 g silica gel. Purification by column chromatography (gradient elution with 0–7.5% MeOH/CH$_2$C$_2$) provided porphyrin 79(33 mg). Further purification of the remaining mixed fractions provided porphyrins 80 (10 mg), and 81 (1 mg). Porphyrin 79: mp200–205° C.; UV-vis λ$_{max}$=456.0 nm, ε=9.50×10$^4$ L/cm-mol; FAB MS m/z=679 [C$_{34}$H$_{32}$MnN$_4$O$_8$]$^+$. Porphyrin 80: mp>300° C.; UV-vis λ$_{max}$=460.0 nm, ε=8.20×10$^4$ L/Cm-mol; FAB MS m/z=665 [C$_{33}$H$_{30}$MnN$_4$O$_8$]$^+$. Porphyrin 81: FAB MS m/z =621 [C$_{32}$H$_{30}$MnN$_4$O$_6$]$^+$.

4. [5-methoxycarbonyl-10,15,20-tris(n-butoxycarbonyl) porphyriato]manganese(III) Chloride (82)

A solution of 78 (20 mg, 0.03 mmol) and MnCl$_2$ (28 mg, 0.22 mmol) in DMF (25 mL) was heated at 140° C. for 1.5 h. Additional MnCl$_2$ (26 mg, 0.21 mmol) was added to the reaction mixture. The reaction mixture was exposed to a stream of air and heating was continued for an additional 4 h. The reaction mixture was cooled to room temperature overnight under a stream of air. Evaporation of DMF provided a solid mixture, which was adsorbed onto 2 g silica gel. Purification by column chromatography (gradient elution with 2–7.5% MeOH/CH$_2$Cl$_2$) provided porphyrin 82 (6 mg): mp 180–185° C.; UV-vis λ$_{max}$=456.0 nm, ε=7.10×10$^4$ L/cm-mol; FAB MS m/z=721 [C$_{37}$H$_{38}$MnN$_4$O$_8$]$^-$.

EXAMPLE 17

XII. [5,15-Bis(ethoxycarbonyl)-10,20-bis(ethyl) porphyrinato]manganese(III) Chloride (50)

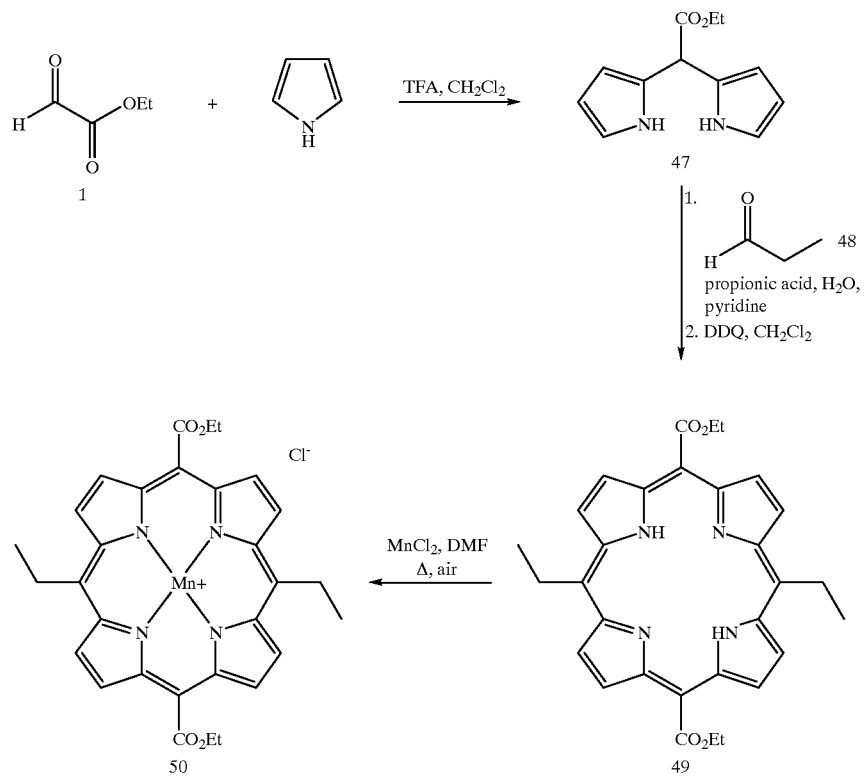

1. meso-(Ethoxycarbonyl)dipyrromethane (47)

In a round-bottom flask equipped with a magnetic stir bar and $N_2$ inlet was placed ethyl glyoxylate (12.6 g, 0.123 mol), pyrrole (102 mL, 1.48 mol) and $CH_2Cl_2$ (700 mL). Trifluoroacetic acid (3.8 mL, 0.049 mol) was then added. The resulting dark solution was stirred overnight at room temperature, transferred into a separatory funnel, diluted with $CH_2Cl_2$, then washed with $H_2O$, saturated aqueous $NaHCO_3$, $H_2O$ and brine. The organic portion was dried ($Na_2SO_4$), filtered and the solvent removed in vacuo. The crude product was repeatedly chromatographed on silica gel (elution with 50% $CH_2Cl_2$/hexanes). Recrystallization from $CH_2Cl_2$/hexane provided the product 47 as white crystals (9.39 g; 35%): mp70–75° C.; $^1$H NMR (300 MHz, $CDCl_3$) δ1.31 (t, 3H), 4.24 (q, 2H), 5.10 (s, 1H), 6.09 (broad s, 2H), 6.16 (m, 2H), 6.72 (broad s, 2H), 8.45 (broad s, 2H).

2. 5,15-Bis(ethoxycarbonyl)-10,20-bis(ethyl)porphyrin (49)

In a foil-covered flask fitted with an air condenser, dipyrromethane 47 (150 mg, 0.687 mmol) was magnetically stirred in propionic acid (5 mL), $H_2O$ (0.2 mL) and pyridine (17 μL) at 90° C. for 5 min (Neya, S.; Funasaki, N. *J Heterocyclic Chem.* 1997, 34, 689–690). Propionaldehyde (25 μL, 0.34 mmol), was added and the reaction mixture was stirred for 40min. Another portion of propionaldehyde (10 μL, 0.14 mmol) was added to the reaction mixture, stirred for 2 h and diluted with $CH_2Cl_2$. The organic phase was washed with $H_2O$, 0.05 N NaOH (2x), and $H_2O$, dried ($Na_2SO_4$), filtered and the solvent was removed in vacuo. The residue was dissolved in $CH_2Cl_2$ (250 mL) and DDQ (108 mg, 0.48 mmol) was added. After stirring overnight, the sample was adsorbed onto silica gel (4 g). Purification by column chromatography (gradient elution 50→100% $CH_2C_2$/hexane) provided porphyrin 46 (12 mg; 10%) as a dark solid: $^1$H NMR (300 MHz, $CDCl_3$) δ1.81 (t, 6H), 2.01 (t, 6H), 5.11–4.99 (m, 8H), 9.44 (d, 4H), 9.54 (d, 4H); FAB MS m/z=511 $[C_{30}H_{30}N_4O_4+H]^+$.

3. [5,15-Bis(ethoxycarbonyl)-10,20-bis(ethyl)porphyrinato]manganese(III) Chloride (50)

To a magnetically stirred solution of porphyrin 49 (12 mg, 0.025 mmol) in anhydrous DMF (4 mL) was added $MnCl_2$ (23 mg, 0.19 mmol). The reaction flask was fitted with a reflux condensor and the solution was heated to 125° C.; air was then pumped into the reaction vessel, and the solution was stirred overnight. The flask was allowed to cool to room temperature, then the solvent was removed in vacuo. The crude material was adsorbed onto silica gel (1 g) and chromatography on silica gel (gradient elution 0→6% $MeOH/CH_2Cl_2$) provided 47 (3.5 mg; 24%) as a dark solid: mp>300° C.; UV-vis $λ_{max}$=462.5 nm, ε=3.43×10$^4$ L/cm-mole; FAB MS m/z=563 $[C_{30}H_{28}MnN_4O_4]^+$.

EXAMPLE 18

Attenuation of Hyperoxic Lung Injury by a Novel Catalitic Antioxidant

Pulmonary toxicity due to hyperoxia is thought to be related to the formation of reactive oxygen species, including superoxide. Increased levels of antioxidant enzymes, such as superoxide dismutases (SOD) and catalase, have been associated with increased survival and adaptation to hyperoxia in rats and mice. The role of acatalytic antioxidant in conferring protection from hyperoxic lung injury to rats was examined. The compound is a manganic porphyrin (AEOL-11201 (see FIG. 1)) with a broad spectrum of antioxidant properties. Male Sprague-Dawley rats were exposed to 100% $O_2$, 635 mmHG, for 7 days. The animals were injected with the compound at 15 mg/kg, or the vehicle intraperitoneally every 24 hours. Perivascular edema, a marker of hyperoxic lung injury, was evaluated on hematoxylin and eosin stained lung sections. Compared to the air control animals, the oxygen exposed group developed significant perivascular edema. AEOL-11201 significantly reduced the edema of small to medium sized vessels in $O_2$ exposed rats. These results indicate that manganic porphyrins are useful as therapeutic antioxidants in disease states in which reactive oxygen species are involved.

What is claimed is:

1. A compound of Formula I or Formula II;

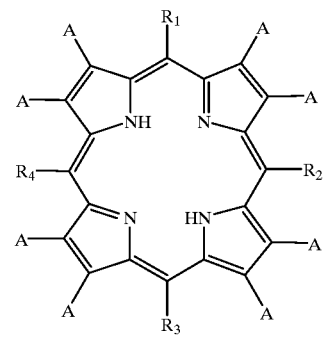

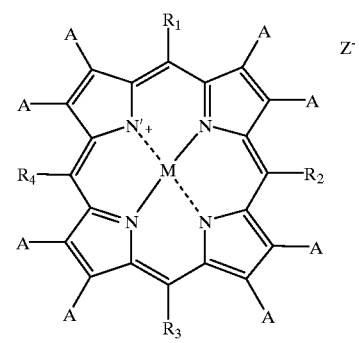

or pharmaceutically acceptable salt thereof, wherein
$R_1$ and $R_3$ are independently:
—$CO_2C_{1-4}$ alkyl; or
—$CO_2(CH_2)_nCX_3$, wherein X is halogen and n=1 to 3;
$R_2$ is:
—H
—$C_{1-4}$alkyl
—COOH
—$CO_2C_{1-4}$ alkyl,
—$CO_2(CH_2)_nCX_3$, wherein X is halogen and n=1 to 3,
—$CON(CH_3)_2$, or
—$CX_3$, wherein X is halogen; and
$R_4$ is:
—H,
—$C_{1-4}$ alkyl
—COOH,
—$CO_2C_{1-4}$ alkyl,
—$CO_2(CH_2)_nCX_3$, wherein X is halogen and n=1 to 3,
—$CON(CH_3)_2$, or
—$CX_3$, wherein X is halogen, and
each A is, independently, hydrogen or halogen,
wherein when said compound is of Formula II, M is a metal selected from the group consisting of manganese, iron, copper, cobalt, nickel and zinc and $Z^-$ is a counterion.

2. The compound according to claim 1 wherein $R_1$ and $R_3$ are, independently, —$CO_2C_{1-4}$alkyl or —$CO_2CH_2CX_3$, $R_2$ is —H, —$CO_2C_{1-3}$alkyl, —$CO_2CH_2CX_3$, —$CON(CH_3)_2$ or $CX_3$ and $R_4$ is —H, —COOH, —$CO_2C_{1-3}$alkyl, —$CON(CH_3)_2$ or —$CX_3$.

3. The compound according to claim 2 wherein $R_1$ and $R_3$ are, independently, —$CO_2C_{1-3}$alkyl, $R_2$ is —$CO_2C_{1-3}$alkyl, —$CON(CH_3)_2$ or —$CX_3$, and $R_4$ is —H, —COOH, —$CO_2C_{1-3}$alkyl, —$CON(CH_3)_2$ or —$CX_3$.

4. The compound according to claim 3 wherein $R_1$ or $R_3$ is —$CO_2CH_3$, —$CO_2CH_2CH_3$, or —$CON(CH_3)_2$, $R_2$ is —$CO_2CH_3$, —$CO_2CH_2CH_3$, or $CX_3$, and $R_4$ is —H, —COOH, —$CO_2CH_3$, —$CO_2CH_2CH_3$ or $CX_3$.

5. The compound according to claim 3 wherein $R_1$, $R_2$ and $R_3$ are, independently, —$CO_2CH_3$ or —$CO_2CH_2CH_3$, and $R_4$ is —H, —COOH, —$CO_2CH_3$ or —$CO_2CH_2CH_3$ or —$CO_2CH_{22}CH_3$.

6. The compound according to claim 5 wherein $R_1$, $R_2$, $R_3$ and $R_4$ are, independently, —$CO_2CH_3$ or —$CO_2CH_2Cl_3$.

7. The compound according to claim 1 wherein at least one A is a halogen.

8. The compound according to claim 1 wherein each A is hydrogen.

9. The compound according to claim 1 wherein said compound is of Formula II and M is manganese.

10. The compound according to claim 1 wherein said compound is of Formula II, M is manganese, $R_1$, $R_2$, $R_3$ and $R_4$ are, independently, —$CO_2CH_3$ or —$CO_2CH_2CH_3$, and each A is a hydrogen.

11. A method of protecting a cell from oxidant-induced toxicity comprising contacting said cell with a protective amount of a compound of Formula I or Formula II:

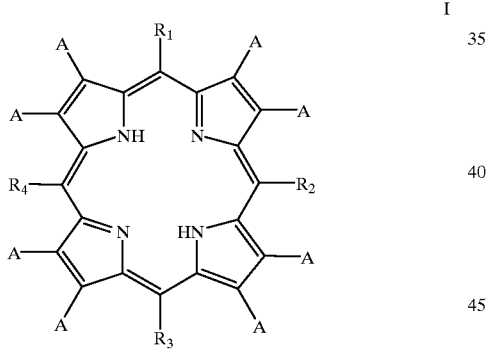

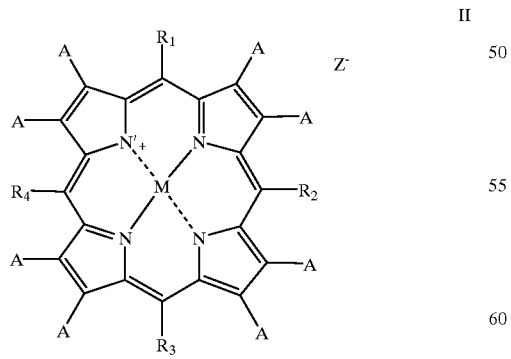

or pharmaceutically acceptable salt thereof, wherein
$R_1$ and $R_3$ are, independently:
—$CO_2C_{1-4}$ alkyl; or
—$CO_2(CH_2)_nCX_3$, wherein X is halogen and n=1 to 3;

$R_2$ is:
—H
—$C_{1-4}$alkyl
—COOH
—$CO_2C_{1-4}$alkyl,
—$CO_2(CH_2)_nCX_3$, wherein X is halogen and n=1 to 3,
—$CON(CH_3)_2$, or
—$CX_3$, wherein X is halogen; and $R_4$ is:
—H,
—$C_{1-4}$alkyl
—COOH,
—$CO_2C_{1-4}$alkyl,
—$CO_2(CH_2)_nCX_3$, wherein X is halogen and n=1 to 3,
—$CON(CH_3)_2$, or
—$CX_3$, wherein X is halogen, and each A is, independently, hydrogen or halogen,
wherein when said compound is of Formula II, M is a metal selected from the group consisting of manganese, iron, copper, cobalt, nickel and zinc and $Z^-$ is a counterion.

12. The method according to claims 11 wherein said compound is of Formula II and M is manganese.

13. The method according to claim 11 wherein said cell is a mammalian cell.

14. A method of treating a patient suffering from a condition that results from or that is exacerbated by oxidant-induced toxicity comprising administering to said patient an effective amount of a compound of Formula I or Formula II:

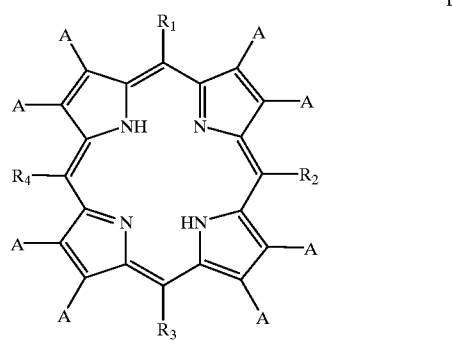

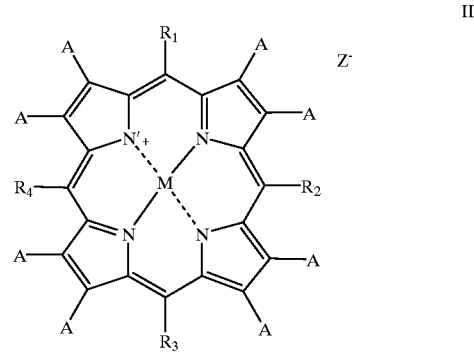

or pharmaceutically acceptable salt thereof, wherein
$R_1$ and $R_3$ are, independently:
—$CO_2C_{1-4}$ alkyl; or
—$CO_2(CH_2)_nCX_3$, wherein X is halogen and n=1 to 3;

R₂ is:
—H
—C$_{1-4}$alkyl
—COOH
—CO$_2$C$_{1-4}$ alkyl,
—CO$_2$(CH$_2$)$_n$CX$_3$, wherein X is halogen and n=1 to 3,
—CON(CH$_3$)$_2$, or
—CX$_3$, wherein X is halogen; and R₄ is:
—H,
—C$_{1-4}$ alkyl
—COOH,
—CO$_2$C$_{1-4}$ alkyl,
—CO$_2$(CH$_2$)$_n$CX$_3$, wherein X is halogen and n=1 to 3,
—CON(CH$_3$)$_2$, or
—CX$_3$, wherein X is halogen, and each A is, independently, hydrogen or halogen,
wherein when said compound is of Formula II, M is a metal selected from the group consisting of manganese, iron, copper, cobalt, nickel and zinc and Z⁻ is a counterion.

15. The method according to claim 14 wherein said compound is of Formula II and M is manganese.

16. A method of treating a pathological condition of a patient that results from a degradation product of NO, comprising administering to said patient an effective amount of a compound of Formula I or Formula II

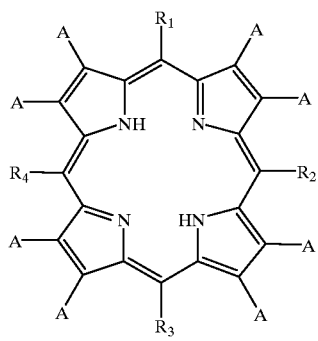

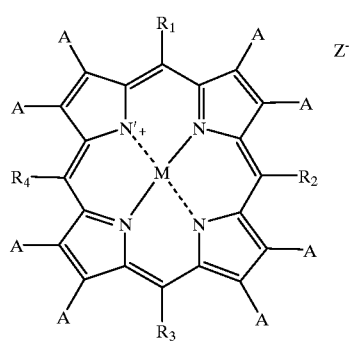

or pharmaceutically acceptable salt thereof, wherein
R₁ and R₃ are, independently;
—CO$_2$C$_{1-4}$ alkyl; or
—CO$_2$(CH$_2$)$_n$CX$_3$, wherein X is halogen and n=1 to 3;
R₂ is:
—H
—C$_{1-4}$ alkyl
—COOH
—CO$_2$C$_{1-4}$ alkyl,
—CO$_2$(CH$_2$)$_n$CX$_3$, wherein X is halogen and n=1 to 3,
—CON(CH$_3$)$_2$, or
—CX$_3$, wherein X is halogen; and R₄ is;
—H,
—C$_{1-4}$alkyl
—COOH,
—CO$_2$C$_{1-4}$ alkyl,
—CO$_2$(CH$_2$)$_n$CX$_3$, wherein X is halogen and n=1 to 3,
—CON(CH$_3$))$_2$, or
—CX$_3$, wherein X is halogen, and each A is, independently, hydrogen or halogen,
wherein when said compound is of Formula II, M is a metal selected from the group consisting of manganese, iron, copper, cobalt, nickel and zinc and Z⁻ is a counterion.

17. The method according to claim 16 wherein said compound is of Formula II and M is manganese.

18. A method of treating a patient for an inflammatory disease comprising administering to said patient an effective amount of a compound of Formula I or Formula II:

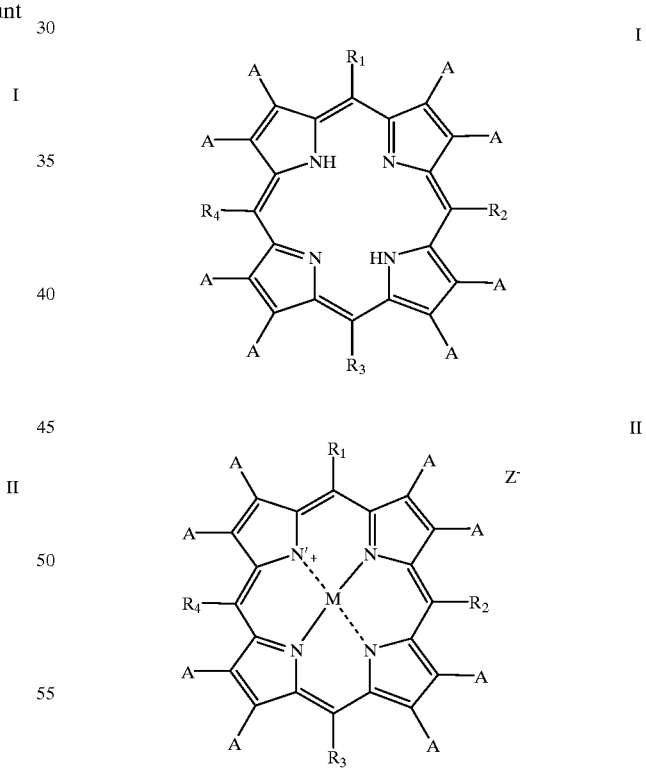

or pharmaceutically acceptable salt thereof, wherein
R₁ and R₃ are, independently:
—CO$_2$C$_{1-4}$ alkyl; or
—CO$_2$(CH$_2$)$_n$CX$_3$, wherein X is halogen and n=1 to 3;
R₂ is,
—H
—C$_{1-4}$alkyl —COOH
—CO$_2$C$_{1-4}$ alkyl,
—CO$_2$(CH$_2$)$_n$CX$_3$, wherein X is halogen and n=1 to 3,
—CON(CH$_3$)$_2$, or
—CX$_3$, wherein X is halogen, and
R$_4$ is:
—H,
—C$_{1-4}$alkyl
—COOH,
—CO$_2$C$_{1-4}$ alkyl,
—CO$_2$(CH$_2$)$_n$CX$_3$, wherein X is halogen and n=1 to 3,
—CON(CH$_3$)$_2$, or
—CX$_3$, wherein X is halogen, and
each A is, independently, hydrogen or halogen,
wherein when said compound is of Formula II, M is a metal selected from the group consisting of manganese, iron, copper, cobalt, nickel and zinc and Z$^-$ is a counterion.

19. The method according to claim 18 wherein said compound is of Formula II and M is manganese.

20. The method according to claim 18 wherein said inflammatory disease is an inflammatory lung disease.

21. The method according to claim 20 wherein said inflammatory lung disease is bronchopulmonary disease.

22. The method according to claim 20 wherein said inflammatory lung disease is asthma.

23. The method according to any one of claims 11, 14, 16 and 18 wherein each A is hydrogen.

* * * * *